United States Patent
Kimoto et al.

(10) Patent No.: US 8,036,615 B2
(45) Date of Patent: Oct. 11, 2011

(54) PORTABLE SIMPLIFIED IMAGE DISPLAY APPARATUS AND RECEIVING SYSTEM

(75) Inventors: Seiichiro Kimoto, Tokyo (JP); Manabu Fujita, Tokyo (JP); Ayako Nagase, Tokyo (JP); Kazutaka Nakatsuchi, Tokyo (JP); Akira Matsui, Tokyo (JP); Toshiaki Shigemori, Tokyo (JP)

(73) Assignees: Olympus Corporation (JP); Olympus Medical Systems Corp. (JP)

( * ) Notice: Subject to any disclaimer, the term of this patent is extended or adjusted under 35 U.S.C. 154(b) by 943 days.

(21) Appl. No.: 11/916,151

(22) PCT Filed: Sep. 1, 2006

(86) PCT No.: PCT/JP2006/317374
§ 371 (c)(1),
(2), (4) Date: Nov. 30, 2007

(87) PCT Pub. No.: WO2007/026890
PCT Pub. Date: Mar. 8, 2007

(65) Prior Publication Data
US 2009/0312604 A1    Dec. 17, 2009

(30) Foreign Application Priority Data

Sep. 2, 2005  (JP) ................ 2005-255495
Sep. 9, 2005  (JP) ................ 2005-263086
Sep. 22, 2005 (JP) ................ 2005-275667

(51) Int. Cl.
*H04B 17/00* (2006.01)
(52) U.S. Cl. ............. 455/226.1; 455/226.4; 455/566
(58) Field of Classification Search .... 455/226.1–226.4, 455/566; 600/300, 103
See application file for complete search history.

(56) References Cited

U.S. PATENT DOCUMENTS

| | | | | |
|---|---|---|---|---|
| 5,950,139 A | * | 9/1999 | Korycan | 455/566 |
| 7,231,186 B2 | * | 6/2007 | Namiki | 455/67.11 |
| 7,367,940 B2 | * | 5/2008 | Fujita et al. | 600/118 |

(Continued)

FOREIGN PATENT DOCUMENTS

JP       2003-019111       1/2003

(Continued)

OTHER PUBLICATIONS

PCT International Search Report and Written Opinion dated Oct. 24, 2006 issued in corresponding PCT International Appln. No. PCT/JP2006/317374 filed Sep. 1, 2006.

(Continued)

*Primary Examiner* — Lana N Le
(74) *Attorney, Agent, or Firm* — Ostrolenk Faber LLP

(57) ABSTRACT

A portable simplified image display apparatus and a receiving system are provided, which can sensuously know the state of received strength of radio signals transmitted from a body-insertable apparatus, in either case of before examination or during examination. A viewer (7) includes a detector that detects received strength of a radio signal transmitted from a capsule endoscope (2) and a notifying unit that notifies the detected state of received strength in a display pattern such as a picture display of a capsule (41). Therefore, in either case of before examination or during examination, the state of received strength of radio signals transmitted from the capsule endoscope (2) can be sensuously known according to the notification result of the state of received strength. If it is during examination, supplementary observation can be performed based on an excellent received image by searching a site having strong received strength, thereby enabling contribution to satisfactory examination.

6 Claims, 28 Drawing Sheets

U.S. PATENT DOCUMENTS

| | | | |
|---|---|---|---|
| 2003/0023150 A1 | 1/2003 | Yokoi et al. | 600/300 |
| 2003/0085994 A1 | 5/2003 | Fujita et al. | |
| 2005/0004473 A1 | 1/2005 | Fujita et al. | 600/476 |
| 2005/0038321 A1 | 2/2005 | Fujita et al. | 600/109 |
| 2005/0159125 A1* | 7/2005 | Lodolo et al. | 455/226.4 |
| 2008/0033257 A1* | 2/2008 | Yokoi et al. | 600/300 |
| 2009/0204181 A1* | 8/2009 | Kawano et al. | 600/113 |

FOREIGN PATENT DOCUMENTS

| | | |
|---|---|---|
| JP | 2003-135387 | 5/2003 |
| JP | 2003-524448 | 8/2003 |
| JP | 2004-128735 | 4/2004 |
| JP | 2004-320396 | 11/2004 |
| JP | 2005-168524 | 6/2005 |
| JP | 2005-218584 | 8/2005 |
| JP | 2005-218703 | 8/2005 |
| JP | 2005-252727 | 9/2005 |
| JP | 2005-253797 | 9/2005 |
| WO | WO 00/22975 | 4/2000 |
| WO | WO 2004/100776 | 11/2004 |
| WO | WO 2005/044094 | 5/2005 |

OTHER PUBLICATIONS

Chinese Office Action dated Nov. 13, 2009 in corresponding Chinese Patent Application No. 200680032124.1 (7 pages).

Japanese Decision of Grant dated Mar. 16, 2010 in corresponding Japanese Patent Application No. 2005-275667 (with English language translation).

International Preliminary Report dated Mar. 13, 2008 for International Patent Application No. PCT/JP2006/317374.

English translation of a Japanese Office Action dated Apr. 14, 2010.

\* cited by examiner

FIG.26

| ANTENNA | RECEIVED STRENGTH | | | | | | | |
| --- | --- | --- | --- | --- | --- | --- | --- | --- |
| SCAN PERIOD | NO.1 | NO.2 | NO.3 | NO.4 | NO.5 | NO.6 | NO.7 | NO.8 |
| AS1 | 80 | 11 | 10 | 9 | 11 | 10 | 9 | 11 |
| AS2 | 80 | 11 | 10 | 9 | 7 | 8 | 6 | 5 |
| AS3 | 7 | 8 | 7 | 6 | 8 | 7 | 6 | 8 |

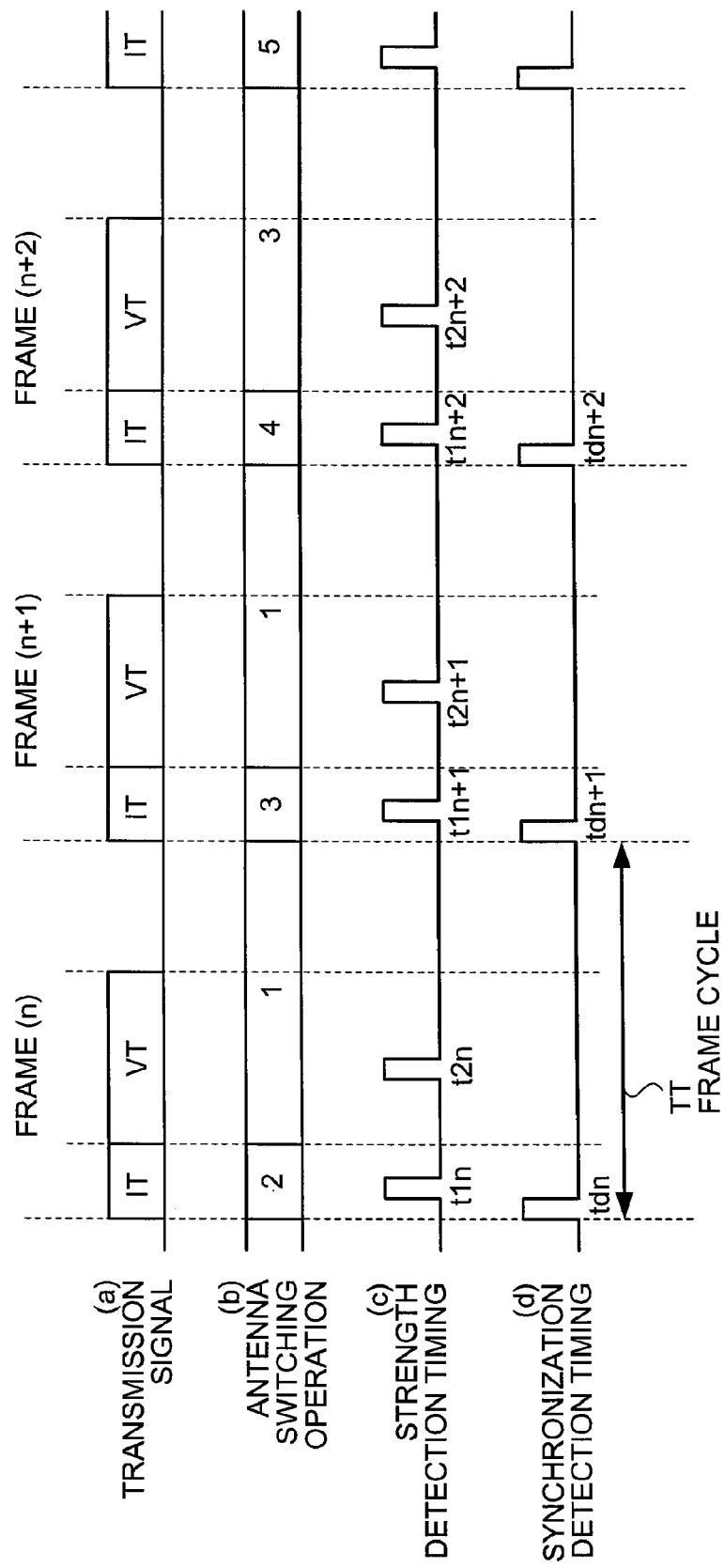

PORTABLE SIMPLIFIED IMAGE DISPLAY APPARATUS AND RECEIVING SYSTEM

CROSS-REFERENCE TO RELATED APPLICATION

The present application is a 35 U.S.C. §§371 national phase conversion of PCT/JP2006/317374, filed Sep. 1, 2006, which claims priority of Japanese Patent Application No. 2005-255495, filed Sep. 2, 2005, Japanese Patent Application No. 2005-263086, filed Sep. 9, 2005, and Japanese Patent Application No. 2005-275667, filed Sep. 22, 2005, the disclosure of which has been incorporated herein by reference. The PCT International Application was published in the Japanese language.

TECHNICAL FIELD

The present invention relates to a portable simplified image display apparatus having an integral antenna that receives a radio signal transmitted from a body-insertable apparatus such as a capsule endoscope to be introduced into a subject, which displays an image based on the received radio signal on a display unit, and a receiving system including the portable simplified image display apparatus.

BACKGROUND ART

Recently, in the field of endoscope, a capsule endoscope equipped with an imaging function and a radio communication function has appeared. This capsule endoscope has a configuration of moving in the internal organs (body cavity) such as esophagus, stomach, and small intestine with peristalsis during an observation period after it is swallowed from a mouth of an examinee as a subject of observation (examination) until it is naturally discharged from a living body (human body) of the examinee, and sequentially taking pictures at a predetermined imaging rate by using the imaging function.

During this observation period while the endoscope is moving in the internal organs, image data acquired in the internal organs by the capsule endoscope is sequentially transmitted to the outside of the examinee by the radio communication function such as radio communications, and stored in a memory provided in an external receiving device. If the examinee carries the receiving device having the radio communication function and the memory function, the examinee swallows the capsule endoscope and then can freely move without any inconvenience even during the observation period until the endoscope is discharged (see Patent Document 1).

When the image data is received, generally in the receiving device, a plurality of antennas is distributed and arranged outside of the examinee for receiving an image signal transmitted from the capsule endoscope, and one antenna having a strong received strength is selected and changed over, to receive the image signal. For example, a receiving device is described in Patent Literature 1, which switches reception of antennas arranged outside of the examinee, to detect the position of the capsule endoscope in the examinee, which is a transmission source of the image signal, based on an electric field strength received by each antenna.

In such a capsule endoscope system, after a series of an imaging operation by the capsule endoscope has been completed, the image data stored in the memory of the receiving device is generally transferred to a workstation or the like, and examination of the image is performed afterwards. However, there are strong demands from doctors for real-time examination of the images of sites such as esophagus and stomach or concerned sites, since the capsule endoscope passes these sites within short time. A system including a simplified image display apparatus that displays images on a real-time basis based on the radio signal transmitted from the capsule endoscope has also been proposed.

A conventional simplified image display apparatus has a configuration capable of electrically connecting to the receiving device, as the simplest configuration, and includes a small display unit and a predetermined signal processor. By having such a configuration, the simplified image display apparatus can input a signal having subjected to reception processing by the receiving device, and after having performed predetermined processing based on the input signal, the simplified image display apparatus displays images taken by the capsule endoscope on the small display unit.

Patent Document 1: Japanese Patent Application Laid-open No. 2003-19111

DISCLOSURE OF INVENTION

Problem to be Solved by the Invention

In the capsule endoscope, it is known that when a site in the body cavity where the capsule endoscope is present at the time of observation is internal organs containing lots of blood, if there is a blood flow between the capsule endoscope and a body surface where the antennas for the receiving device are arranged, radio waves from the capsule endoscope are hardly transmitted to the body surface side. However, since several antennas for the receiving device are arranged discretely and fixedly on several sites on the body surface of the examinee, even if the antenna having the strongest received strength is selected, there can be a portion having a weak received strength depending on the position of the capsule endoscope.

Therefore, it has been considered to have such a configuration that the simplified image display apparatus is made in a portable size holdable by an operator and includes an antenna integrally, to perform observation by receiving the signal by the antenna at a site having a strong received strength, avoiding a site where the radio waves from the capsule endoscope are hardly transmitted, and the simplified image display apparatus itself receives the radio signals from the capsule endoscope supplementarily, while changing the position of the antenna, and displays the images, thereby enabling direct examination on the site.

However, when the simplified image display apparatus is formed in a portable size holdable by the operator, the size of the display unit formed of an LCD or the like becomes considerably smaller than the size of the display unit on the workstation or the like. Accordingly, even if the position of the simplified image display apparatus is changed, while watching the displayed image on the small display unit, it is difficult to determine whether the currently displayed image is an image at a site having the strong received strength, and hence real-time observation cannot be ensured in a state having the strong received strength.

Further, depending on the capsule endoscope, there can be an abnormal capsule endoscope, in which an output state of the radio signal transmitted by the capsule endoscope itself is bad and the received strength on the receiving device side is originally weak. Conventionally, however, no effective measure is taken to remove a capsule endoscope, which has such abnormality and cannot be used for the examination, before the examination (before being swallowed).

The present invention has been achieved to solve the above problems, and it is an object of the present invention to provide a portable simplified image display apparatus and a receiving system, which can sensuously know the state of received strength of the radio signals transmitted from a body-insertable apparatus, in either case of before examination or during examination, and can contribute to satisfactory examination.

Means for Solving Problem

A portable simplified image display apparatus according to one aspect of the present invention has includes a display unit, an integral antenna that receives a radio signal transmitted from a body-insertable apparatus to be introduced into a subject and displays an image according to the radio signal on the display unit; a detector that detects a received strength of the radio signal transmitted from the body-insertable apparatus; and a notifying unit that notifies the state of received strength detected.

In the portable simplified image display apparatus, the notifying unit may notify the state of the received strength by visually changing the state of the received strength according to the received strength detected.

In the portable simplified image display apparatus, the notifying unit may use a part of the display unit, and notify the state of the received strength in a predetermined display pattern changing depending on the received strength detected.

Further, in the portable simplified image display apparatus, the notifying unit may use a light emission element, and notify the state of the received strength in a predetermined light-on display pattern changing depending on the received strength detected.

In the portable simplified image display apparatus, the notifying unit may notify the state of the received strength by aurally changing the state of the received strength according to the received strength detected.

The portable simplified image display apparatus may further include a built-in memory that stores image data according to the radio signal received.

A receiving system according to another aspect of the present invention includes a receiving device carried by a subject for receiving a radio signal transmitted from a body-insertable apparatus inserted into the subject by an antenna arranged relative to the subject and storing image data according to the radio signal in a memory, and a portable simplified image display apparatus detachably connected to the receiving device to display an image according to the radio signal received by the receiving device on a display unit. The portable simplified image display apparatus includes an integral antenna that receives a radio signal transmitted from the body-insertable apparatus, an image display unit that displays an image according to the radio signal received by the antenna on the display unit, a detector that detects the strength of the radio signal transmitted from the body-insertable apparatus and received by the antenna, and a notifying unit that notifies the state of received strength detected.

In the receiving system, the notifying unit may notify the state of the received strength by visually changing the state of the received strength according to the received strength detected.

In the receiving system, the notifying unit may use a part of the display unit, and notify the state of the received strength in a predetermined display pattern changing depending on the received strength detected.

Further, in the receiving system, the notifying unit may use a light emission element, and notify the state of the received strength in a predetermined display pattern changing depending on the received strength detected.

In the receiving system, the notifying unit may notify the state of the received strength by aurally changing the state of the received strength according to the received strength detected.

In the receiving system, the portable simplified image display apparatus may further include a built-in memory that stores image data according to the radio signal received.

Effect of the Invention

According to the portable simplified image display apparatus and the receiving system according to the present invention, since the portable simplified image display apparatus includes the detector that detects the received strength of the radio signal transmitted from the body-insertable apparatus, and the notifying unit that notifies the detected state of received strength, the received strength of the radio signals transmitted and output from the body-insertable apparatus can be sensuously known according to the notification result of the state of received strength, in either case of before examination or during examination. In the case of before the examination, it can be prevented beforehand an abnormal body-insertable apparatus originally having a weak received strength from being swallowed, and in the case of during the examination, supplementary observation can be performed based on an excellent received image by searching a site having strong received strength, thereby enabling contribution to satisfactory examination.

BRIEF DESCRIPTION OF DRAWINGS

FIG. 26 shows a specific example of a received strength detection result by the synchronization-recovering-antenna switching process;

FIG. 30 is a time chart of the antenna switching process when the synchronization signal is received.

EXPLANATIONS OF LETTERS OR NUMERALS

Figure 1:
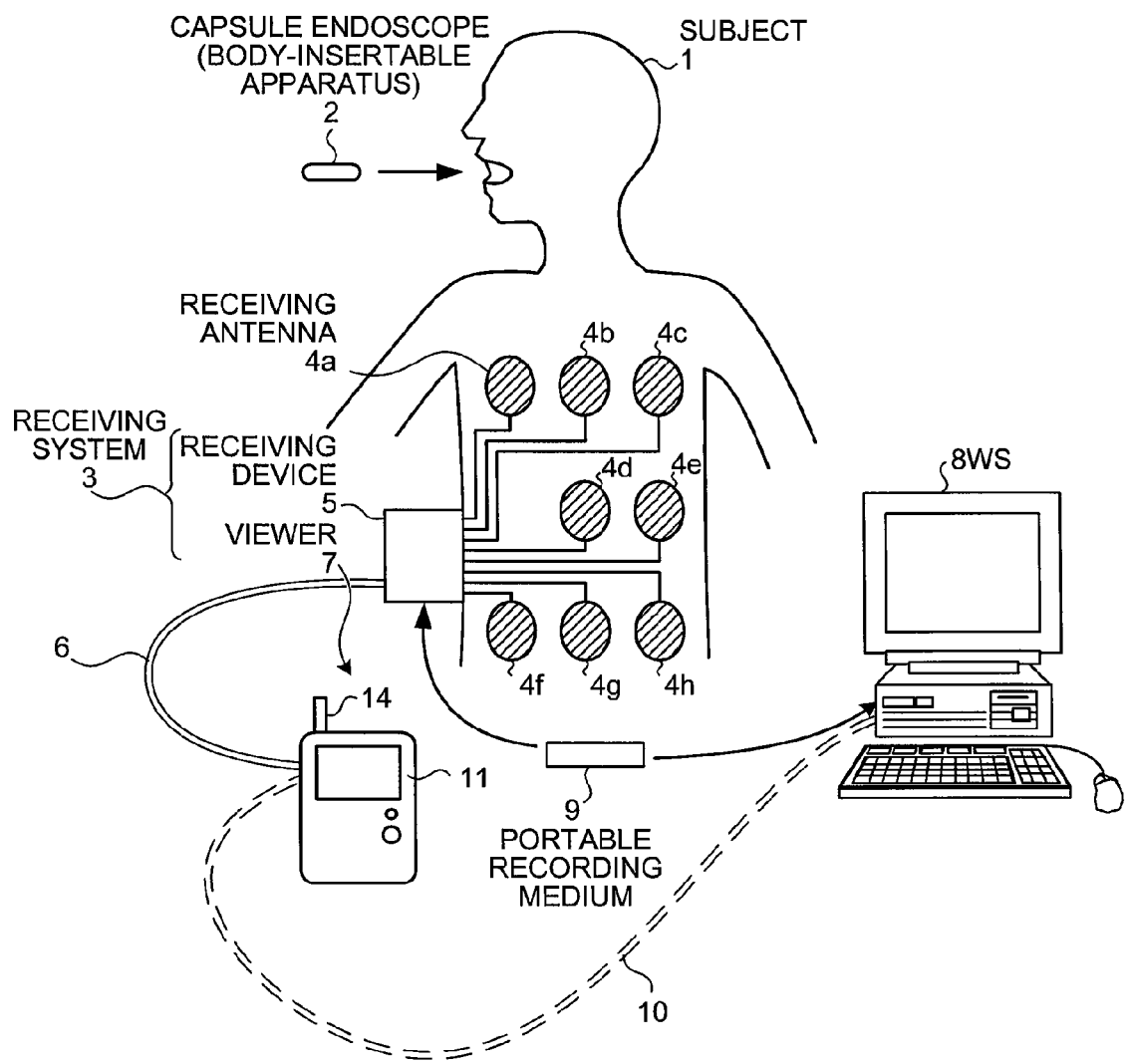
FIG. 1 is a schematic diagram of an overall configuration of a wireless intra-subject information acquiring system according to a first embodiment, which is a preferable embodiment of a portable simplified image display apparatus and a receiving system according to the present invention.

1 Subject
2 Capsule endoscope
3 Receiving system
4a to 4h Receiving antenna (Set antenna)
2 Receiving device
7 Viewer
9 Portable recording medium
11 Display unit
14 Antenna
41 Picture display of capsule
43 LED

BEST MODE(S) FOR CARRYING OUT THE INVENTION

Exemplary embodiments of the present invention will be explained below in detail with reference to the accompanying drawings. Note that the present invention is not limited to the embodiments, and the embodiments can be variously modified within the range of the scope of the present invention.

First Embodiment

Figure 2:
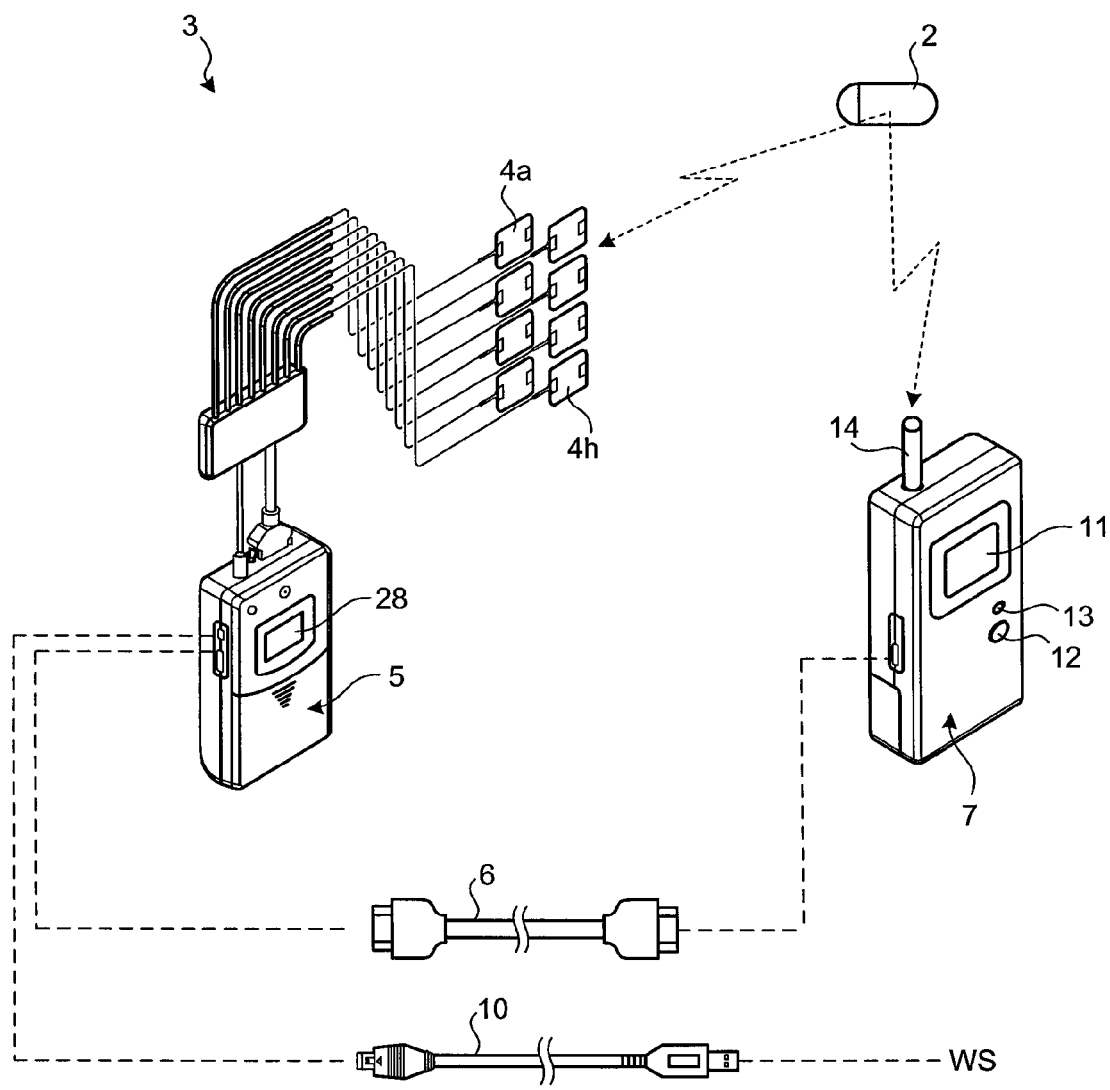
FIG. 2 is an exploded perspective view of a configuration example of the receiving system.

FIG. 1 is a schematic diagram of an overall configuration of a wireless intra-subject information acquiring system, which is a preferable embodiment of the portable simplified image display apparatus and the receiving system according to the present invention, and FIG. 2 is an exploded perspective view of a configuration example of the receiving system. The wireless intra-subject information acquiring system uses a capsule endoscope as one example of the body-insertable apparatus, which is a transmitting unit. In FIG. 1, the wireless intra-subject information acquiring system includes a receiving system 3 used for receiving a radio signal transmitted from a capsule endoscope 2 introduced into a subject 1. The receiving system 3 includes a receiving device 5 used in a state carried by the subject 1 to receive a radio signal received via set antennas (receiving antennas) 4a to 4h, and a viewer 7 as the portable simplified image display apparatus detachably connected to the receiving device 5 by a viewer cable 6 to display an image taken by the capsule endoscope 2, based on an electric signal output from the receiving device 5.

The wireless intra-subject information acquiring system according to the first embodiment further includes a workstation (WS) 8 that displays an image of the body cavity based on a image signal received by the receiving system 3, a portable recording medium 9 as a storage unit for performing transfer of data between the receiving device 5 and the workstation 8, and a detachable communication cable 10 for transmitting data from the viewer 7 to the workstation 8.

The capsule endoscope 2 is introduced into the subject 1 via a mouth of the subject 1 and has a function for performing wireless transmission of the image data of the body cavity acquired by, for example, a built-in imaging mechanism to the outside of the subject 1. The set antennas 4a to 4h are distributed and fixedly arranged at appropriate positions on the body surface of the subject 1. These set antennas 4a to 4h are provided, for example, on a receiving jacket wearable by the subject 1, and the subject 1 carries the set antennas 4a to 4h by wearing the receiving jacket. In this case, the set antennas 4a to 4h can be detachable relative to the jacket.

The workstation 8 is for displaying images of the body cavity imaged by the capsule endoscope 2, and displays images based on data acquired by the portable recording medium 9 or the like. Specifically, the workstation 8 can have a configuration such that images are directly displayed by a CRT display, a liquid crystal display, or the like, or a configuration such that images are output to other media, like a printer.

As the portable recording medium 9, a CompactFlash® Memory or the like is used, which is detachable relative to the receiving device 5 and the workstation 8, and has a structure capable of outputting or recording information at the time of being set in both the receiving device 5 and the workstation 8. In the first embodiment, the portable recording medium 9 is set in a display device of the workstation 8, for example, before examination, to store identification information such as an examination ID, and immediately before examination, is set in the receiving device 5 and the identification information is read by the receiving device 5 and registered in the receiving device 5. While the capsule endoscope 2 is moving in the body cavity of the subject 1, the portable recording medium 9 is set in the receiving device 5 attached to the subject 1, to record data transmitted from the capsule endoscope 2. After the capsule endoscope 2 is discharged from the subject 1, that is, after imaging inside of the subject 1 has finished, the portable recording medium 9 is taken out from the receiving device 5 and set in the workstation 8, so that the workstation 8 reads the data recorded on the portable recording medium 9. For example, since transfer of data between the receiving device 5 and the workstation 8 is performed by the portable recording medium 9, the subject 1 can freely moves during taking pictures of the body cavity, which also contributes to reduction of transfer period of data between the receiving device 5 and the workstation 8. The transfer of data between the receiving device 5 and the workstation 8 can be performed by using another recording unit built in the receiving device 5, for example, a hard disk, and the receiving device 5 and the workstation 8 can be connected by wire or wirelessly for data transfer between the receiving device 5 and the workstation 8.

The viewer 7 is a portable type formed in a size holdable by an operator by hand, and has a function for displaying an image based on the electric signal output from the receiving device 5. To achieve such a function, the viewer 7 includes a display unit 11 by means of a small LCD for image display. Reference numeral 12 denotes a power switch, and 13 denotes a pilot lamp lighted on at the time of operating the viewer. The viewer 7 has an integral rod-like antenna 14 for achieving a reception function for directly receiving a radio signal transmitted from the capsule endoscope 2, not via the receiving device 5. In FIG. 1, although the receiving device 5 and the viewer 7 are connected with each other via the viewer cable 6, both are not always used in the connected state. When real-time observation by using the image received by the receiving device 5 is not performed, the viewer cable 6 is detached, and the subject 1 carries only the receiving device 5.

Figure 3:
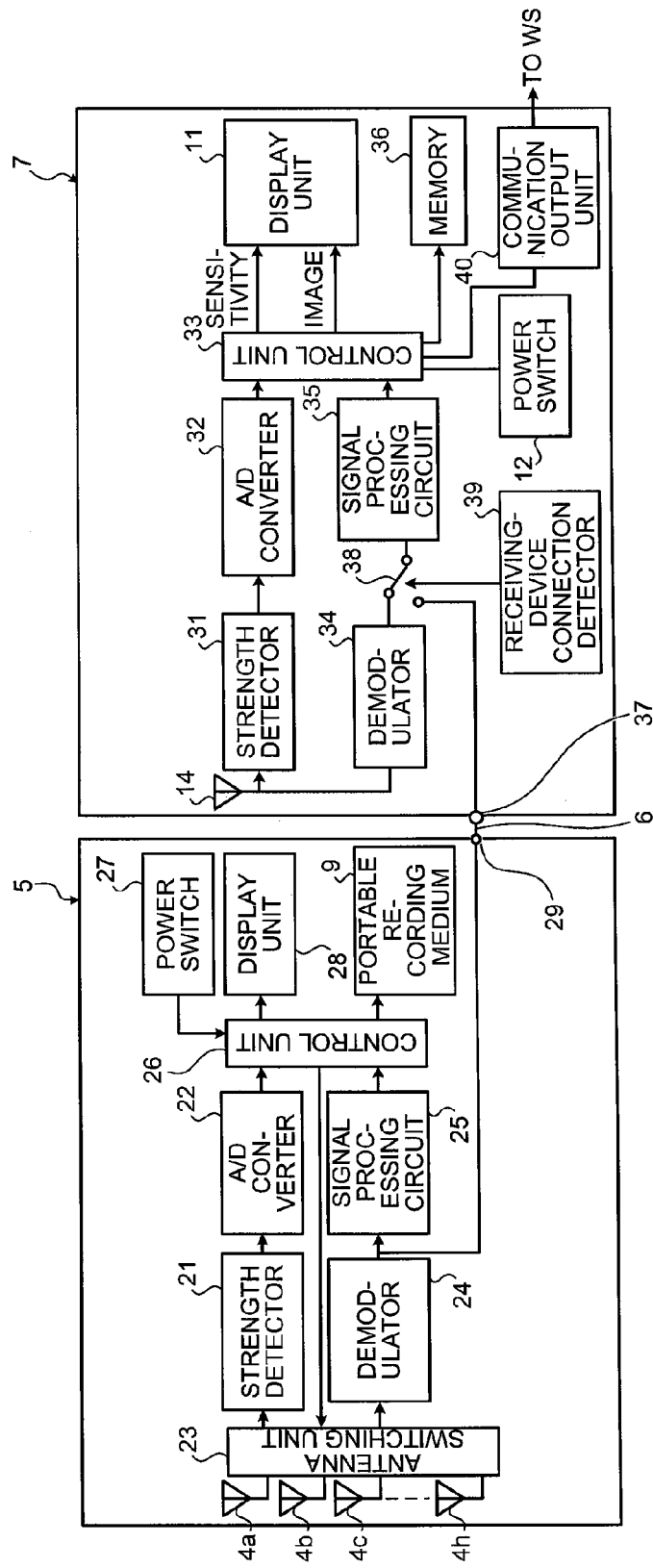
FIG. 3 is a schematic block diagram of a configuration example of a receiving device and a viewer constituting the receiving system according to the first embodiment.

The configuration of the receiving device 5 and the viewer 7 is explained next in detail. FIG. 3 is a schematic block diagram of a configuration example of the receiving device 5 and a viewer 7 constituting the receiving system 3 according to the first embodiment. The receiving device 5 includes a strength detector 21 that detects received strength of respective set antennas 4a to 4h based on a received strength signals from the set antennas 4a to 4h, an A/D converter 22 that A/D-converts a detection result of the received strength, and an antenna switching unit 23 that selects one antenna having the highest received strength from the set antennas 4a to 4h based on the A/D-converted detection result of the received strength. The receiving device 5 further includes a demodulator 24 that demodulates the radio signal received via the one antenna selected by the antenna switching unit 23, and a signal processing circuit 25 for performing predetermined image processing with respect to the demodulated electric signal. Further, the receiving device 5 includes a control unit 26 having a microcomputer configuration, including a CPU or the like that controls the entire receiving device 5. To the control unit 26 are connected a power switch 27, a small display unit 28, and the portable recording medium 9, in addition to the A/D converter 22, the antenna switching unit 23, and the signal processing circuit 25. Further, the receiving device 5 has a cable connector 29, to which the viewer cable 6 is connected, branched from an output side of the demodulator 24. Although not shown, a battery for driving respective units is built therein or provided by external connection.

The viewer 7 includes a strength detector 31 formed of a sample-hold circuit or the like for detecting the received strength based on the received strength signal from the antenna 14, an A/D converter 32 that A/D-converts a detection result of the received strength, and a control unit 33 that evaluates the detection result of the A/D-converted received strength. The viewer 7 further includes a demodulator 34 that demodulates the radio signal received via the antenna 14, and a signal processing circuit 35 for performing predetermined image processing with respect to the demodulated electric signal. The control unit 33 having a microcomputer configuration including a CPU or the like that controls the entire viewer 7 is connected to a power switch 12, a display unit 11, and a built-in memory 36 in addition to the A/D converter 32 and the signal processing circuit 35. Further, a changeover switch 38 that selectively switches an output side of the demodulator 24 or a cable connector 37 side connecting to the viewer cable 6 relative to the signal processing circuit 35 is provided, and a receiving device connection detector 39 that controls switching of the changeover switch 38 is provided. A communication output unit 40 that outputs data to the workstation 8 via a communication cable 10 is connected to the control unit 33. Although not shown, a battery for driving respective units is built therein.

Figure 4:
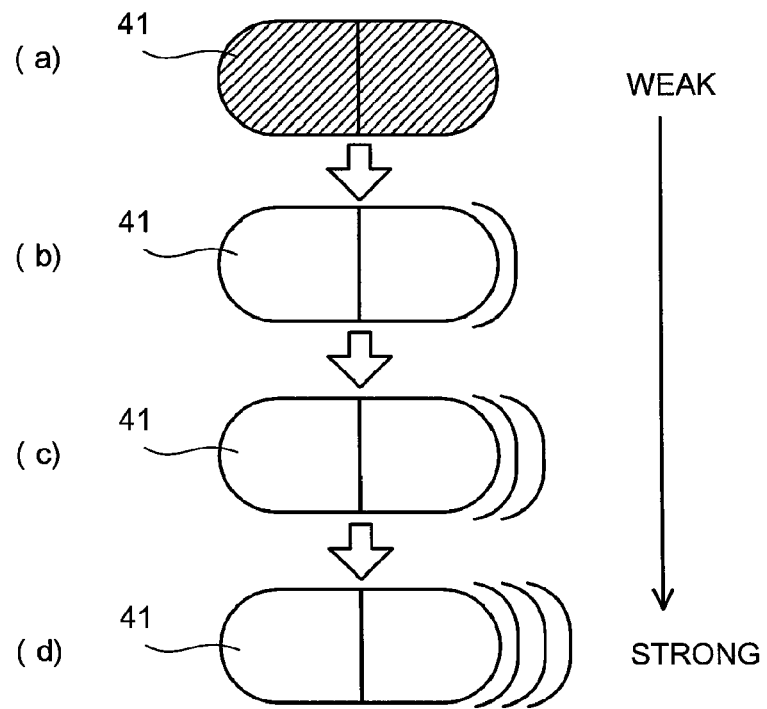
FIG. 4 is a schematic diagram of a pattern example of a picture display of a capsule showing a received strength.

In the viewer 7 in the first embodiment, a part of the display unit 11 is used as a notifying unit under control of the control unit 33, so as to notify the state of received strength to an operator in a predetermined display pattern changing depending on the detected received strength. For example, when the received strength is divided into four levels between weak and strong intensities, as shown in FIG. 4, a part of the display unit 11 is used to display the received strength by changing a pattern of a picture-display-of-capsule 41. FIG. 4(a) indicates a case of received strength 0, and displayed by red (hatched in the figure) indicating a warning by the picture-display-of-capsule 41. As the received strength becomes stronger as shown in FIGS. 4(b) to 4(d), the pattern visually and stepwise displays a state where the received strength increases by increasing the number of graphic radio lines one by one.

A basic operation of the wireless intra-subject information acquiring system according to the first embodiment is explained below. The capsule endoscope 2 introduced into the subject 1, with the built-in power switch being turned on, takes pictures at a predetermined interval, while sequentially moving in the body cavity, and transmits the acquired image data to the outside as a radio signal. A plurality of set antennas 4a to 4h are arranged on the body surface of the subject 1, and a reception signal received by the antenna having the strongest received strength, among the reception signals transmitted from the capsule endoscope 2, is demodulated by the demodulator 24. The image data subjected to predetermined image processing by the signal processing circuit 25 is stored in the portable recording medium 9 sequentially. At this time, if the viewer 7 is connected by the viewer cable 6, the changeover switch 38 is switched to the viewer connector 37 side, and the image data of the body cavity received by the receiving device 5 is displayed on the display unit 11 of the viewer 7 on the real-time basis, thereby enabling real-time observation. Thereafter, the capsule endoscope 2 is discharged outside of the subject 1, and upon completion of the examination, the portable recording medium 9 is taken out from the receiving device 5, and set in the workstation 8 side. Accordingly, the image data of the body cavity recorded on the portable recording medium 9 is displayed on a large display screen of the workstation 8, thereby enabling detailed examination by a doctor and the like.

The operation of the viewer 7 according to the first embodiment is explained next. The viewer 7 in the first embodiment has an integral antenna 14, so that the viewer 7 can directly receive the radio signal transmitted from the capsule endoscope 2, not via the receiving device 5, and can detect the received strength, thereby enabling notification of the state of received strength in a predetermined display pattern, by using a part of the display unit 11.

Figure 5:
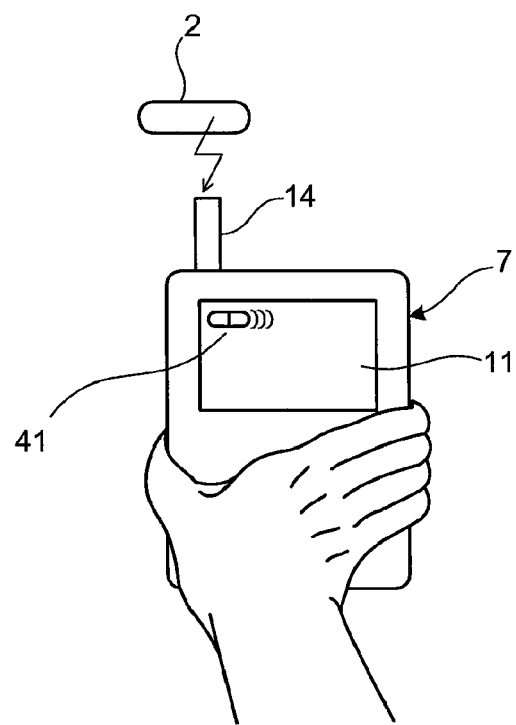
FIG. 5 is a front elevation showing a state where the received strength of a capsule endoscope before examination is detected.

For example, before the examination, as shown in FIG. 5, a doctor or a nurse holds a single viewer and brings it close to the capsule endoscope capsule endoscope 2 before being swallowed, with the power switch being turned on, to receive the radio signal from the capsule endoscope 2 directly through the antenna 14, thereby detecting the received strength thereof. Since the detected state of received strength is displayed as the picture-display-of-capsule 41 on the display unit 11 of the viewer 7, the state of received strength relative to the capsule endoscope 2 can be known visually and sensuously. At this time, when the capsule endoscope 2 is abnormal such that the transmission output strength is originally weak and the received strength is also weak, for example, not only in the case of the picture-display-of-capsule 41 as shown in FIG. 4(a), but also in the case of the picture-display-of-capsule 41 as shown in FIG. 4(b) or 4(c), the examination cannot be performed in an excellent state. Therefore, swallowing of the capsule endoscope can be avoided beforehand, and the capsule endoscope 2 can be changed to a normal capsule endoscope 2 having strong received strength, thereby contributing to an excellent examination.

Figure 6:
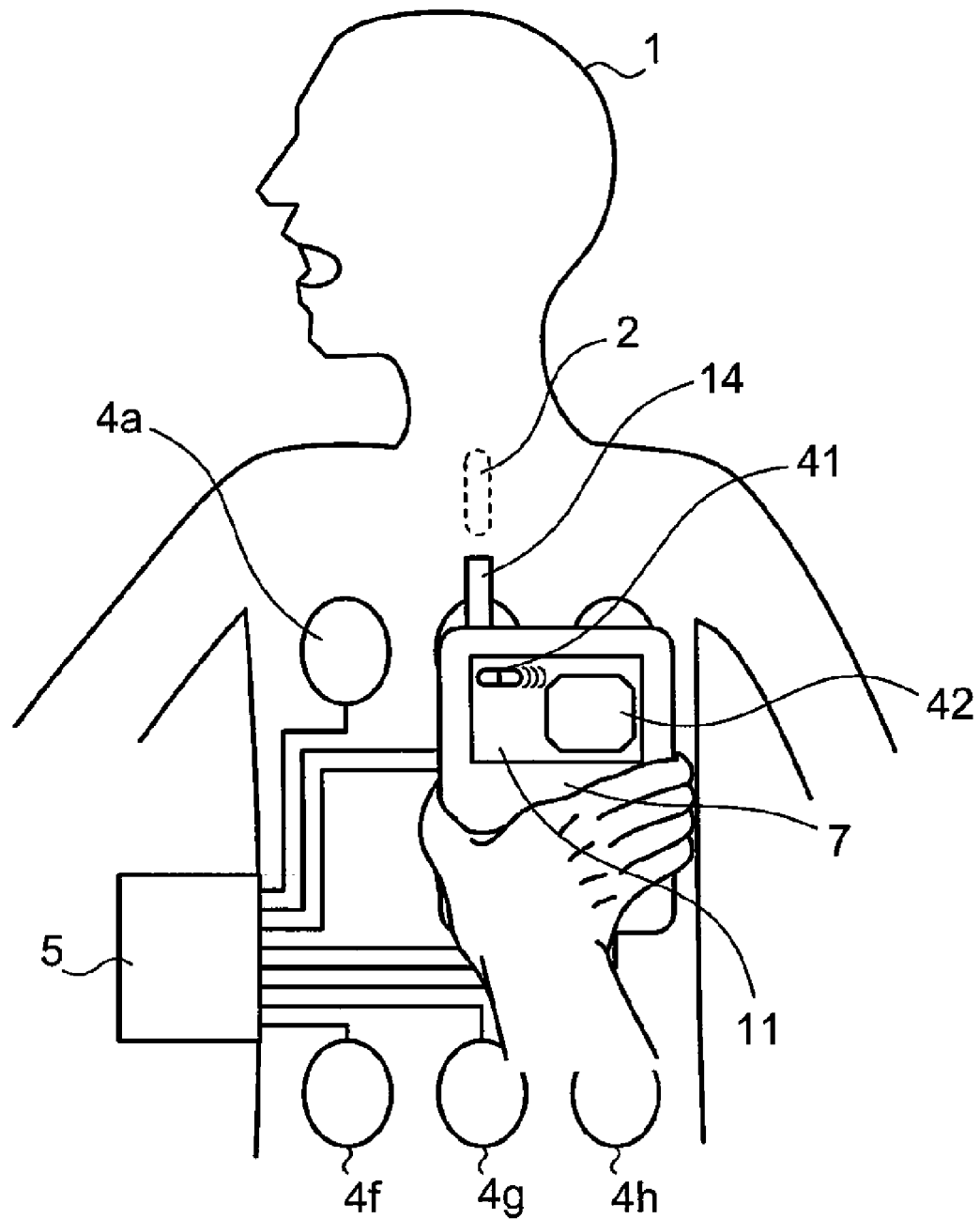
FIG. 6 is a front elevation showing a state where the received strength of the capsule endoscope during examination is detected.

Immediately after starting examination, for example, when the capsule endoscope 2 passes through the esophagus and the stomach, the doctor holds the viewer 7 in the single state, as shown in FIG. 6, according to need, to bring the viewer 7 close to the subject 1, thereby to receive a radio signal from the capsule endoscope 2 via the antenna 14 supplementarily, concurrently with the set antennas 4a to 4h. Accordingly, the image data of the body cavity can be directly acquired, not via the receiving device 5, and displayed on the display unit 11 of the viewer 7 as an image 42 acquired by the capsule. At this time, the received strength of the radio signal from the capsule endoscope 2 has been detected by the control unit 33 via the strength detector 31 and the A/D converter 32, and the detected state of received strength is displayed on a part of the display unit 11 in the pattern of the picture-display-of-capsule 41. Accordingly, the received strength level at the position of the antenna 14 can be known visually and sensuously. Therefore, by moving the position of the antenna 14 by changing the position of the viewer 7, a position where the highest received strength can be acquired, for example as shown in FIG. 4(d), is searched out. Accordingly, the radio signal from the capsule endoscope 2 can be received in the best state without being affected by the blood flow, and supplementary observation for supplementing the original observation by the set antennas 4a to 4h and the receiving device 5 can be favorably performed.

At the time of such an operation, the image data from the capsule endoscope 2 received through the antenna 14 is used for the display on the display unit 11, through the demodulator 34 and the signal processing circuit 35, and on the other hand, the image data is sequentially stored in the built-in memory 36, associated with the received strength at that time. Direct acquisition of the image data from the capsule endoscope 2 by the viewer 7 is supplementary in a specific region such as the esophagus and the stomach, and since a memory capacity of the portable recording medium 9 is not required, the built-in memory 36 can do the job. After the supplementary observation by the viewer 7 has finished, the viewer 7 is connected to the workstation 8 by the communication cable 10, and the image data of the body cavity stored in the built-in memory 36 is transmitted to the workstation 8 through the communication output unit 40. Accordingly, the image data of the body cavity can be used appropriately for the examination, together with the original image data of the body cavity over the whole examination time acquired by the portable recording medium 9, and contribute to excellent examination.

Figure 7:
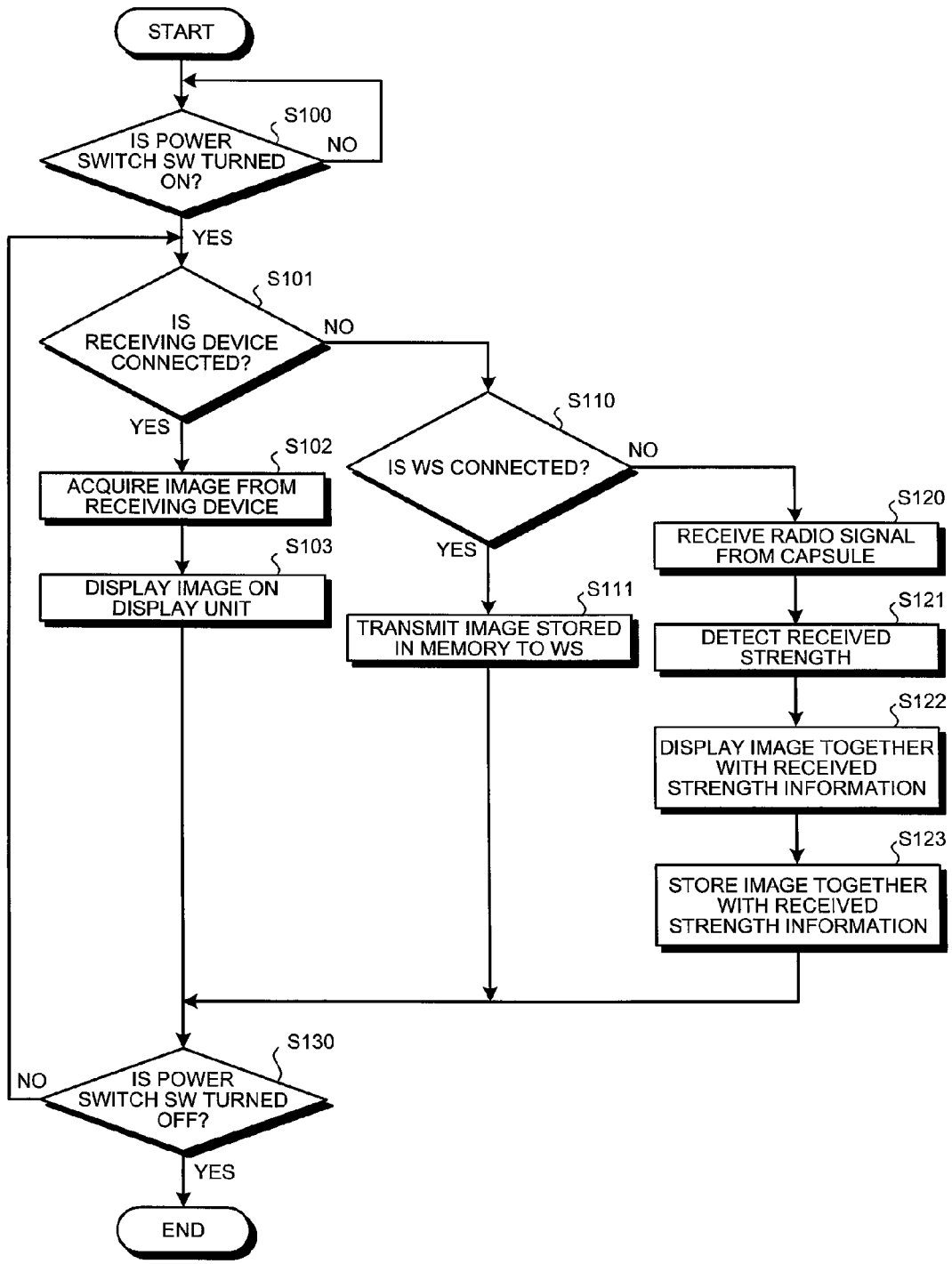
FIG. 7 is a schematic flowchart of an operation control example corresponding to a connection state of the viewer.

FIG. 7 is a schematic flowchart of an operation control example corresponding to a connection state of the viewer 7 executed by the control unit 33. The processing control is executed in a state in which the power switch 12 of the viewer 7 is turned on (step S100: Yes). At first, it is determined whether the receiving device is connected based on the detection result of the receiving device connection detector 39 (step S101). When the receiving device 5 is connected to the viewer 7 by the viewer cable 6 (step S101: Yes), the viewer 7 functions as a monitor of the receiving device 5, and the image data is acquired from the receiving device 5 on the real-time basis (step S102), and the acquired image is displayed on the display unit 11 on the real-time basis (step S103). Accordingly, real-time observation through the receiving device 5 is achieved.

On the other hand, when the receiving device 5 is not connected to the viewer 7 (step S101: No), it is determined whether the workstation (WS) 8 is connected to the viewer 7 by the communication cable 10 (step S110). When the workstation 8 is connected to the viewer 7 (step S110: Yes), the image data stored in the built-in memory 36 is transmitted to the workstation 8 through the communication output unit 40 (step S111).

Further, when the viewer 7 is in the single state without being connected to the receiving device 5 or the workstation 8 (step S110: No), the radio signal from the capsule endoscope 2 is received through the antenna 14 (step S120), and the received strength at the time is detected (step S121). The received image of the body cavity is real-time displayed on the display unit 11, together with the picture display of the capsule 41 indicating the state of received strength (step S122), and the image data of the body cavity is sequentially stored in the built-in memory 36 associated with the received strength at that time (step S123). Such processing control is repeated until the power switch 12 is turned off (step S130: Yes).

In the first embodiment, the state of received strength is visually informed by the picture display of the capsule 41, which is a predetermined display pattern using the part of the display unit 11. However, the display pattern is not limited thereto, and the display pattern can be such that lightness and darkness of a back light at portions other than the image 42 acquired by the capsule on the display unit 11 in the LCD configuration are changed in a stepwise manner from light to dark, corresponding to the weak to strong level of the received strength.

Figure 8:
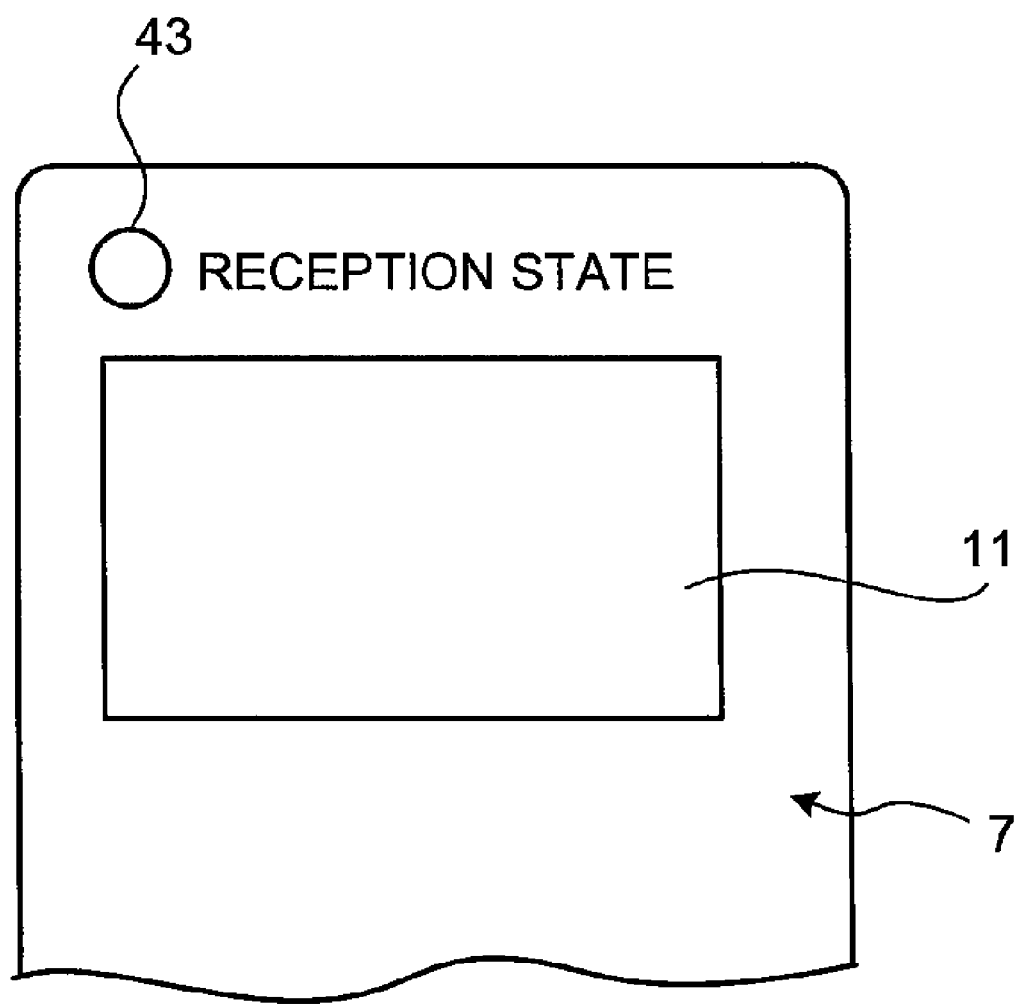
FIG. 8 is a schematic front elevation of a modification example using an LED.

As shown in FIG. 8, the light emission element for notifying the reception state, for example an LED 43 is added outside of the display unit 11, and the LED 43 can be controlled so as to light on in a predetermined light-on display pattern corresponding to the weak to strong level of the received strength. For example, a light-on display pattern can be such that in a state in which the received strength is considerably weak, red light is blinked by the LED 43 to give a warning, in a state in which the received strength does not reach a predetermined threshold level, red light is lighted on by the LED 43 to draw attention, and in a state in which the received strength is equal to or higher than the predetermined threshold level, green light is lighted on by the LED 43.

Further, not only the visual notification, but also a notification method such that a speaker or the like is built in the viewer 7, and aural sound is changed in a stepwise manner, with the length thereof being changed, such as "Pip", "Pip-Pip", and "Pip-Pip-Pip", or "Peep", "Peeep", and "Peeeep", corresponding to the weak to strong level of the received strength can be used.

Second Embodiment

Figure 9:
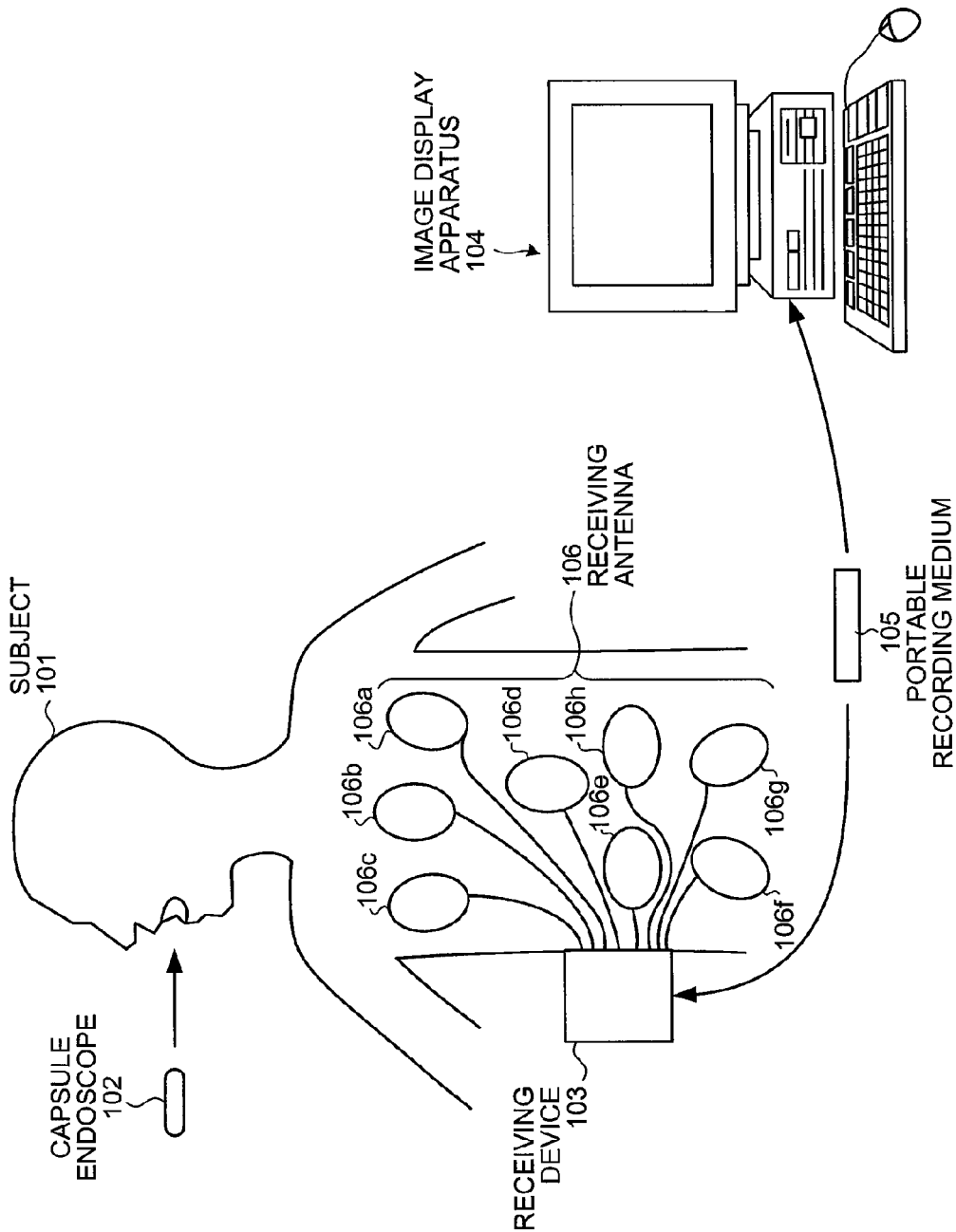
FIG. 9 is a schematic diagram of a configuration of the wireless intra-subject information acquiring system according to a second embodiment of the present invention.

The wireless intra-subject information acquiring system according to a second embodiment is explained next. FIG. 9 is a schematic diagram of an overall configuration of the wireless intra-subject information acquiring system. The wireless intra-subject information acquiring system uses a capsule endoscope as one example of the body-insertable apparatus.

As shown in FIG. 9, the wireless intra-subject information acquiring system includes a capsule endoscope 102 introduced into a subject 101 for wirelessly transmitting imaged image data of images of inside of the subject to a receiving device 103, the receiving device 3 that receives the image data wirelessly transmitted from the capsule endoscope 102, an image display apparatus 104 that displays images of inside of the subject based on an image signal received by the receiving device 103, and a portable recording medium 105 that transfers image data and the like between the receiving device 103 and the image display apparatus 104.

The receiving device 103 includes a receiving antenna 106 having a plurality of antennas 106a to 106h adhered to the body surface of the subject 101. The receiving device 103 receives image data and the like wirelessly transmitted from the capsule endoscope 102 via the receiving antenna 106, and records the received image data in correspondence with received strength information of each antenna 106a to 106h at the time of receiving the image data.

The antennas 106a to 106h are achieved, for example, by using a loop antenna, and arranged at predetermined positions on the body surface of the subject 101, that is, at positions corresponding to respective internal organs inside the subject 101, which is a passage route of the capsule endoscope 102. Alternatively, the antennas 106a to 106h can be arranged at predetermined positions on a jacket or the like worn by the subject 101. In this case, the antennas 106a to 106h are arranged at the predetermined positions on the body surface of the subject 101 via the jacket or the like. Arrangement of the antennas 106a to 106h can be optionally changed according to the purpose of observation and diagnosis of the inside of the subject 101. The number of antennas included in the receiving antenna 106 is not necessarily eight shown as the antennas 106a to 106h, and can be more or less than eight.

The image display apparatus 104 is achieved, for example, by a workstation including a CRT, a liquid crystal display or the like, and performs image display based on the image data acquired via the portable recording medium 105 or the like. The image display apparatus 104 can output image data to an output unit such as a printer and display the image data. The image display apparatus 104 can include a communication function with external devices, so as to acquire or output image data by wire communication or wireless communication.

The portable recording medium 105 is achieved by CompactFlash® Memory, CD, DVD, or the like, is detachable relative to the receiving device 103 and the image display apparatus 104, and can output or record various pieces of information such as image data when the portable recording medium 105 is set in the receiving device 103 or the image display apparatus 104. The portable recording medium 105 is set in the receiving device 103, for example, while the capsule endoscope 102 is introduced into the subject 101, and records the image data received by the receiving device 103 from the capsule endoscope 102. Further, after the capsule endoscope 102 is discharged from the subject 101, the portable recording medium 105 is taken out from the receiving device 103 and set in the image display apparatus 104, to output the recorded image data to the image display apparatus 104. Thus, since transfer of data between the receiving device 103 and the image display apparatus 104 is performed by the portable recording medium 105, the subject 101 can freely moves while the capsule endoscope 102 is introduced therein. The transfer of data between the receiving device 103 and the image display apparatus 104 can be performed by wire communication or wireless communication.

Figure 10:
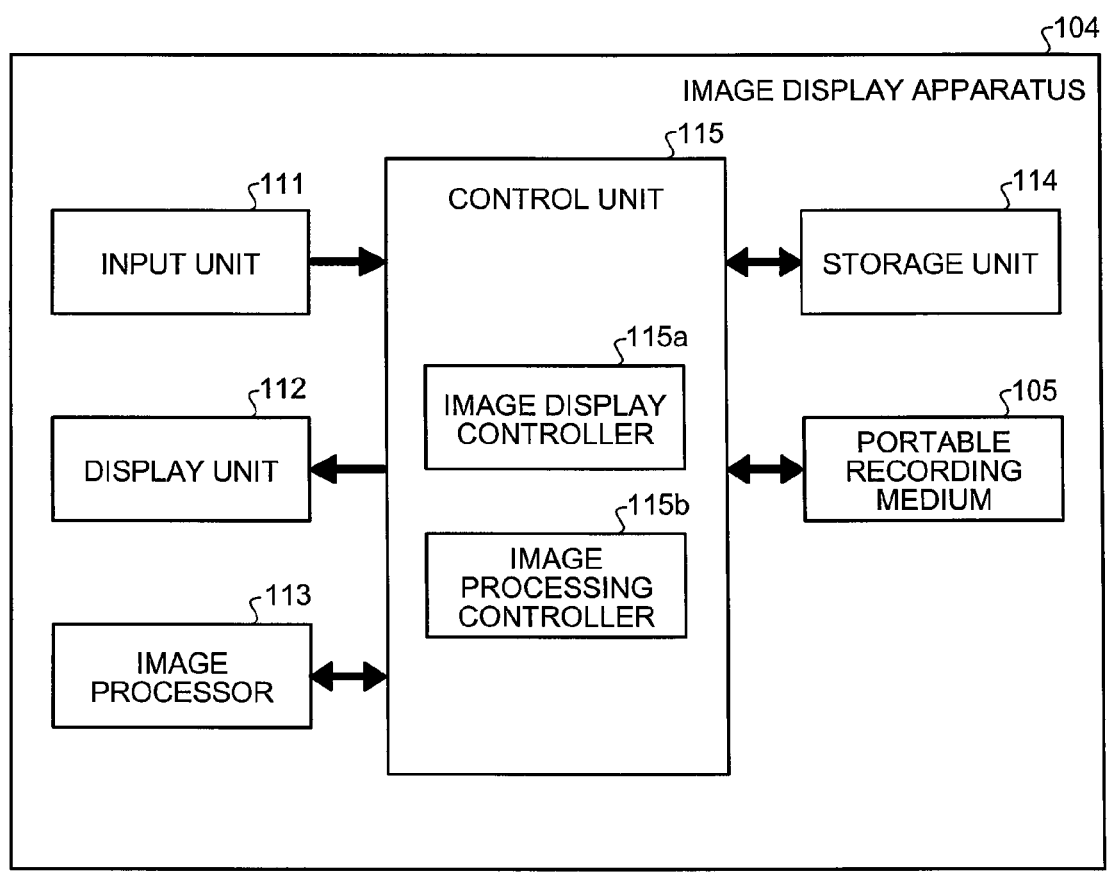
FIG. 10 is a block diagram of a configuration of an image display apparatus according to the second embodiment of the present invention.

A configuration of the image display apparatus 104 according to the second embodiment is explained next. FIG. 10 is a block diagram of the configuration of the image display apparatus 104. As shown in FIG. 10, the image display apparatus 104 includes an input unit 111 that inputs various pieces of information, a display unit 112 that displays various pieces of information, an image processor 113 that processes the input image, a storage unit 114 that stores various pieces of information, and a control unit 115 that controls processing and operations of respective units in the image display apparatus 104. The input unit 111, the display unit 112, the image processor display unit 113, and the storage unit 114 are electrically connected to the control unit 115. The image display apparatus 104 further includes an interface corresponding to the portable recording medium 105, and is equipped with the portable recording medium 105 detachably. The portable recording medium 105 at the time of attachment is electrically connected to the control unit 115.

The input unit 111 has various switches, input keys, a mouse, and a touch panel, to input various types of processing information such as selection information of a display image. An observer of the display image as an operator of the image display apparatus 104 can perform various operations such as read, selection, and recording of the display image via the input unit 111. The input unit 111 can include a wired or wireless communication interface such as USB or IEEE1394, so as to input an image from an external device.

The display unit 112 includes a liquid crystal display or the like, and displays various pieces of information such as image data. The display unit 112 displays various data such as image data stored in the portable recording medium 105 or the storage unit 114, and a graphical user interface (GUI) screen, on which an input request or the like of various pieces of processing information is made relative to the observer and the like of the image display apparatus 104.

The storage unit 114 is achieved by a ROM which stores various processing programs beforehand, and a RAM which stores processing parameters for respective processing, processing data, and the like.

The image processor 113 acquires image data from the portable recording medium 105 or the storage unit 114 based on the control by an image processing controller 115b, and performs various types of image processing such as density conversion (gamma conversion or the like), smoothing (noise reduction or the like), sharpening (edge highlight or the like), and image recognition (detection of a feature image area, calculation of an average color, or the like), relative to the acquired image data.

The control unit 115 is achieved by a CPU or the like that executes various processing programs stored in the storage unit 114. The control unit 115 particularly includes an image display controller 115a and the image processing controller 115b. The image display controller 115a controls such that a series of images taken at a plurality of points in time are displayed on the display unit 112 as the image data stored in the portable recording medium 105 or the storage unit 114. In the second embodiment, as the series of images, a series of images of the subject acquired by taking pictures of various internal organs of the subject 101 at a plurality of points in time are displayed.

The image display controller 115a further displays an antenna having the largest received strength in correspondence with the arrangement of the plurality of antennas included in the receiving device 103 for each main display image, by referring to the received strength information associated with the image, and displays the antenna having the largest received strength identifiably from other antennas. Specifically, the image display controller 115a displays an antenna layout drawing graphically indicating the arrangement of the antennas 106a to 106h on the subject 101, together with the image inside the subject mainly displayed, and displays any one of the antennas 106a to 106h on the antenna layout drawing as the antenna having the largest received strength. At this time, the image display controller 115a displays the antenna having the largest received strength identifiably from other antennas among the antennas 106a to 106h.

The image processing controller 115b acquires image data stored in the portable recording medium 105 or the storage unit 114, outputs the acquired image data to the image processor display unit 113, and controls various types of image processing relative to the output image. The image processing controller 115b further outputs the image data as the processing result in the image processor 113 to the storage unit 114 or the portable recording medium 105 so as to be stored therein.

Figure 11:
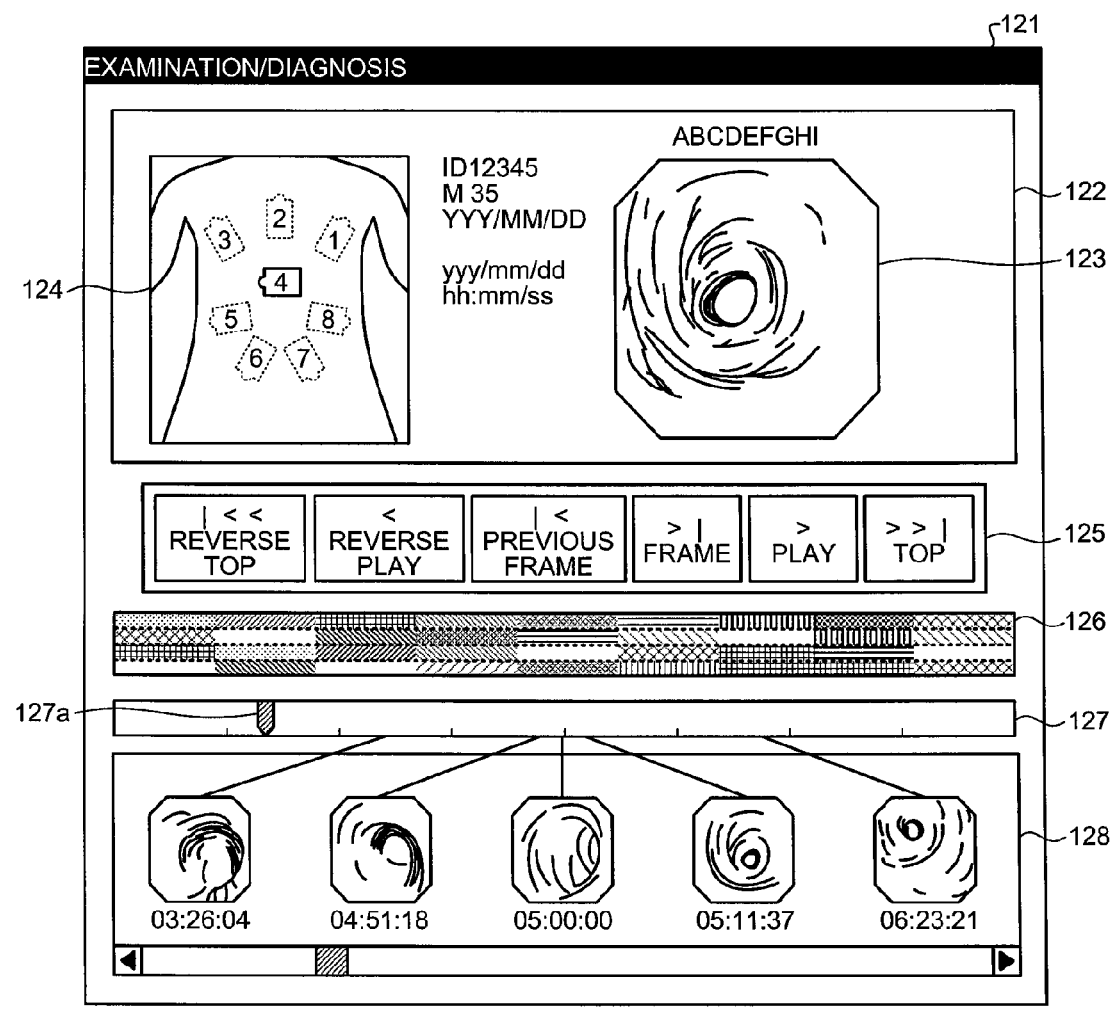
FIG. 11 shows a display screen displayed by the image display apparatus shown in FIG. 9.

The display screen (GUI screen) displayed on the display unit 112 by the image display apparatus 104 is explained next. FIG. 11 is one example of the GUI screen displayed by the image display apparatus 104 based on the control of the image display controller 115a. As shown in FIG. 11, a window 121 ("examination/diagnosis" window) as the GUT screen is displayed on the display unit 12. In the window 121, a main display area 122 in which a main display image or the like is displayed, an image operation area 125 in which various image operation buttons indicated as icons are displayed, a color bar 126 and a time bar 127 as time scales indicating an imaging period of the series of images of the subject, and a display subarea 128 in which thumbnails or the like are displayed in parallel on the display screen in this order from the top to the bottom.

In the main display area 122, a main display image 123, which is an image selected from the series of images of the subject based on instruction information input form the input unit 111, and an antenna layout drawing 124 graphically indicating the arrangement of the antennas 106a to 106h on the subject 101 are displayed. Further, name, ID number, sex, age, birth date, imaged date, imaged time and the like of the subject 101 associated with the image of the subject selected as the main display image 123 are displayed in the main display area 122 as character information. A predetermined number (two or more) of main display images can be displayed in the main display area 122 corresponding to a predetermined operation.

Arrangement of the antennas 106a to 106h are graphically displayed together with a part of profile of the subject 101 in the antenna layout drawing 124. In the antenna layout drawing 124, an antenna number as an identification number of each antenna is character-displayed near the antennas 106a to 106h. For example, in FIG. 11, "1" to "8" are shown as the antenna number.

In the color bar 126, an average color as a whole of each image included in the series of images of the subject is displayed in time series. That is, the average color of the images of the subject taken at each point in time is displayed in the display area of the point in time on the color bar 126. Since the images of the subject have average colors of different types corresponding to the imaged internal organs, the observer and the like can easily identify the internal organs imaged in the image of the subject at each point in time, from transition of the average colors along the time axis on the color bar 126.

Further, the color bar 126 is configured such that the whole display area is vertically divided into four on the display screen, and the average colors of the divided image areas corresponding to the images of the subject are displayed in time series in each divided color bar. In other words, the average color of each image of the subject is calculated for each divided image area acquired by vertically dividing the whole image area into four, and the average color of each divided image area in correspondence with a dividing order is displayed, in the color bar 126, for each divided display area acquired by vertically dividing the display area at each point in time into four.

According to such a color bar 126, the observer and the like can easily recognize not only the internal organs taken in the images of the subject at each point in time, but also the state of the imaged internal organs corresponding to the imaged range, from the transition of the average colors along the time axis of the color bars in divided stages. Accordingly, since the average color of black in the image area including, for example, a luminal part and the average color of other image areas are displayed in the color bars in different stages, the observer and the like can recognize the state of the internal organs in the imaging range excluding the luminal part.

In the time bar 127, a slider 127a movable in the direction of time axis on the time bar 127 is displayed. The slider 127a indicates the imaging time of the image of the subject displayed as the main display image 123 on the timer bar 127, and moves on the time bar 127, synchronously with a display changeover of the main display image 123. For example, when any one of the image operation buttons in the image operation area 125 is operated by a mouse or the like (not shown), the main display image 123 is changed over and displayed, and the slider 127a moves to a position indicating the imaging time of the image of the subject displayed as the main display image 123, after the display is changed over.

On the contrary, when the slider 127a is moved by the mouse or the like (not shown), the image of the subject corresponding to the imaging time indicated by the slider 127a is displayed as the main display image 123, after the slider 127a has been moved. When the slider 127a is continuously moved, the main display image 123 is changed over and displayed continuously, following the movement of the slider 127a. According to such a slider 127a, the observer and the like can immediately display the image of the subject as the main display image 123, by moving the slider 127a to the imaging time corresponding to the subject image of a desired internal organ, found by referring to, for example, the color bar 126.

The left ends of the color bar 126 and the time bar 127 as the time scales indicate the imaging time of the first image in the time series of the series of images of the subject, and the right ends indicate the imaging time of the last image in the time series. Normally, the imaging time at the left end corresponds to the time at which reception of image data is started by the receiving device 103, and the imaging time at the right end corresponds to the time at which reception of image data has finished.

In the display subarea 128, an image selected and extracted from the series of images of the subject is displayed as the thumbnail. Specifically, for example, in response to a predetermined button operation or a mouse operation, the image of the subject displayed as the main display image 123 at the operating time is additionally displays in the display subarea 28 as the thumbnail.

In the display subarea 128, additional information such as imaging time is displayed as character information near the respective thumbnail. The additional information displayed as the character information can be changed over according to a predetermined operation, and can be not displayed. In the display subarea 128, a line segment associating the respective thumbnail with the imaging time of the respective thumbnails indicated on the time bar 127 is displayed.

Since there is a limitation on the size of the display area in the display subarea 128, a predetermined number of thumbnails can be displayed collectively. For example, in FIG. 11, an example in which maximum 5 thumbnails can be displayed collectively is shown. When the number of the extracted thumbnails is larger than the predetermined number that can be collectively displayed, the thumbnails exceeding the predetermined number are changed over and displayed according to the operation of a scroll bar displayed in the display subarea 128. Further, the thumbnails displayed in the display subarea 128 are displayed as the main display image 123 in response to the predetermined button operation or the mouse operation.

Display control of the antenna layout drawing 124 in the image display apparatus 104 according to the second embodiment is explained here. As shown in FIG. 11, the image display controller 115a refers to the received strength information by the antennas 106a to 106h associated with the image of the subject displayed as the main display image 123, and displays the antenna having the largest received strength identifiably from other antennas on the antenna layout drawing 124. For example, in FIG. 11, an antenna having an antenna number "4" is displayed as the antenna having the largest received strength identifiably from other antennas.

As the identifiable display control, specifically, the image display controller 115a controls such that display brightness of the antenna having the largest received strength in the antenna layout drawing 124 is differentiated from other antennas. In this case, it is desired that the display brightness of the antenna having the largest received strength is brighter than that of the other antennas. Further, the image display controller 115a can display such that a display tone or a display chroma of the antenna having the largest received strength is made different from that of other antennas, instead of differentiating the display brightness. When the display tone is made different, for example, the display color of the antenna having the largest received strength is set as green, which has normally a high relative luminosity factor, and other antennas can be displayed by colors such as magenta, red, and blue, which have a largely different color tone from that of green. The image display controller 115a can also control the display such that two or more of the display brightness, display tone, and display chroma are made different. Further, the image display controller 115a can display antennas identifiably from each other by making the shape and size of the antennas different from each other.

The antenna having the largest received strength displayed based on the display control of the image display controller 115a can be easily identified from other antennas and recognized by the observer and the like. Therefore, by the image display apparatus 104 according to the second embodiment, objective information based on the received strength information of the receiving antenna 106 and the receiving position information of respective antennas 106a to 106h included in the receiving antenna 106 can be displayed, and recognized easily by the observer and the like.

By acquiring the position information of the antenna having the largest received strength in the image of the subject displayed as the main display image 123, the observer and the like can estimate the position of the capsule endoscope 102 at the time of imaging the image of the subject, that is, an imaging portion in the subject 101 based on the position information. Further, by estimating the imaging portion, misrecognition of the imaging portion by the observer and the like, based on uncertain position information acquired by calculation using the received strength of a plurality of antennas and displayed, can be prevented.

The image display controller 115a can display a diagram indicating the arrangement of the internal organs in the subject 101 in the antenna layout drawing 124, overlapped on a part of a profile image of the subject 101, so as to facilitate estimation of the imaging portion by the observer and the like.

In the display control of the antenna layout drawing 124 by the image display controller 115a, when the display position of the antenna having the largest received strength is momentarily changed corresponding to changeover of display of the image of the subject to be displayed as the main display image 123, it can be difficult for the observer and the like to recognize the position of the antenna having the largest received strength immediately before the changeover of display. In correspondence with this, the image display controller 115a can control such that the antenna having the largest received strength is displayed by using an afterimage effect in visual observation.

Figure 12:
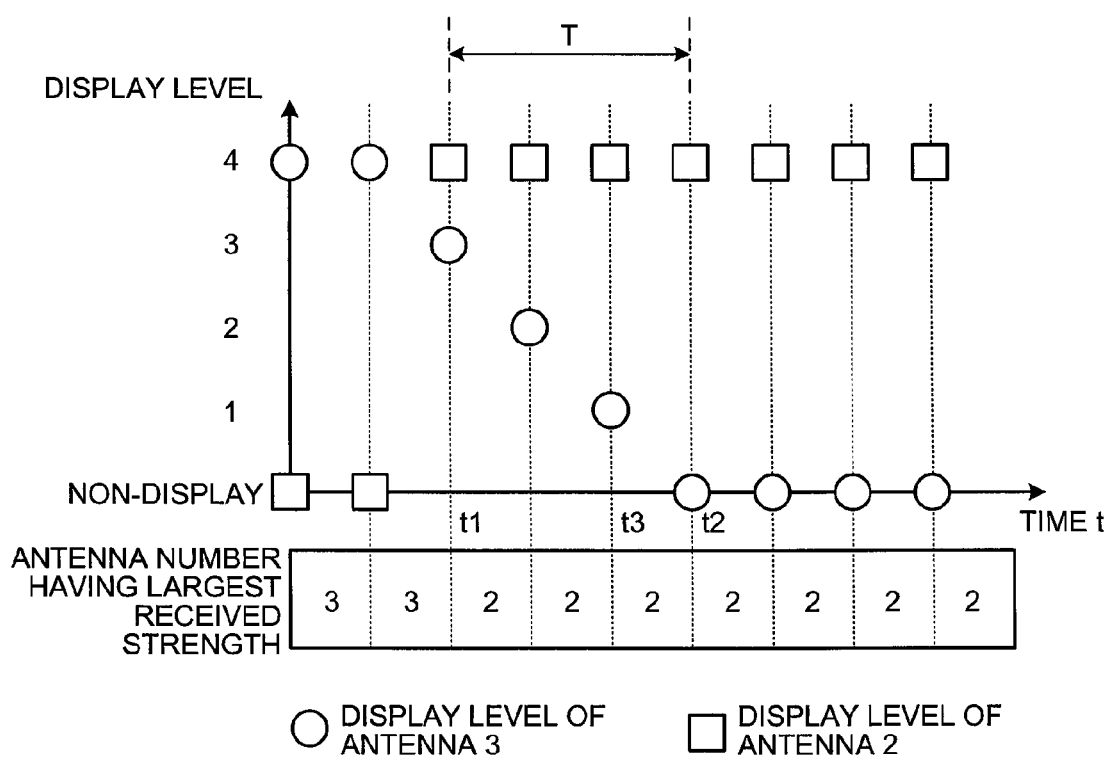
FIG. 12 is an explanatory diagram of a display control method of an antenna having the largest received strength using an afterimage effect.

FIG. 12 is a conceptual diagram explaining a display control method of the antenna having the largest received strength using the afterimage effect. As shown in FIG. 12, the image display controller 115a controls such that when the display of the antenna having the largest received strength is changed over, for example, from an antenna having an antenna number "3" (hereinafter, antenna "3") to an antenna having an antenna number "2" (hereinafter, antenna "2"), antenna "3" is continuously displayed at a display level different from that of antenna "2" only for predetermined time period T (=t2−t1) from the display changeover time t1.

More specifically, the image display controller 115a continuously displays antenna "3" at a display level lower than that of antenna "2" during the period T, and attenuates the display level of antenna "3" in a stepwise manner. In this case, the image display controller 115a controls the display such that antenna "3" is not displayed at time t2 when the period T has passed since the display changeover time t1. "Not displayed" here means that the display level becomes the same as that of other antennas excluding antenna "2" and antenna "3".

For example, in FIG. 12, at the display changeover time t1, the antenna having the largest received strength is changed over from antenna "3" to antenna "2", and corresponding to this, the display level of antenna "2" is set to the maximum level (level 4), and the display level of antenna "3" is changed to level 3, which is one level lower than the maximum level. Further, during the period T from the display changeover time t1 to time t2, the display level of antenna "3" is attenuated in a stepwise manner, and becomes a non-display level at time t2.

Figure 13:
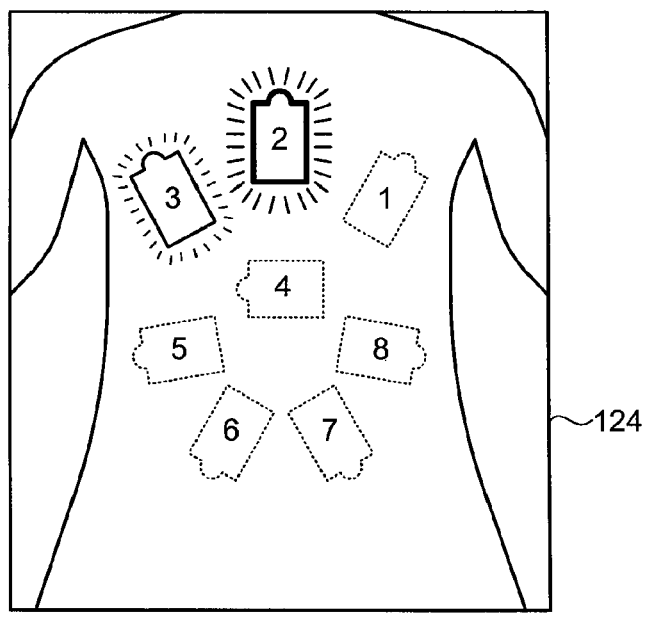
FIG. 13 shows an antenna layout drawing displayed by using the display control method shown in FIG. 12.

FIG. 13 shows a display state of the antenna layout drawing 124 at time t3 shown in FIG. 12. At time t3, as shown in FIG. 12, the display level of antenna "2" as the antenna having the largest received strength is at the maximum level, and the display level of antenna "3" is level 1 lower than the maximum level. In the antenna layout drawing 124, for example, as shown in FIG. 13, antenna "2" is displayed at the maximum brightness setting, and antenna "3" is displayed at a display brightness darker than the maximum brightness but brighter than the non-display level, corresponding to the respective display levels. The display level to be differentiated between the antennas having the largest received strength before and after the display changeover is not limited to the display brightness, and can be display tone or display chroma. Further, two or more of the display brightness, display tone, and display chroma can be made different.

Thus, by controlling the display level of the antenna having the largest received strength by the image display controller 115a, the observer and the like can recognize both the antenna having the largest received strength at the current time and the antenna having the largest received strength immediately before the display changeover time t1, during the predetermined time period T since the display changeover time t1, even if the display of the antenna having the largest received strength is changed over. Further, the observer and the like can discriminate which antenna has the largest received strength at the current time. In this case, the observer and the like recognize the antenna having the largest received strength before changeover of the display as an afterimage during the period T.

In the display control method in the antenna layout drawing 124, the image display controller 115a displays only the antenna having the largest received strength identifiably from other antennas, however, the received strength information of respective antennas 106a to 106h can be displayed.

Figure 14:
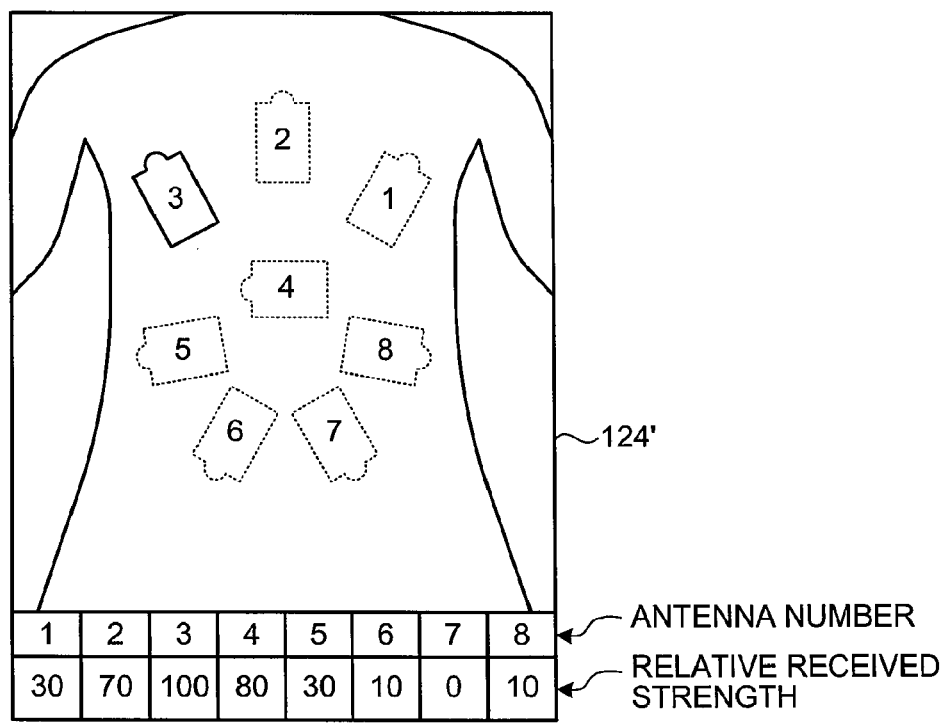
FIG. 14 shows an antenna layout drawing in which relative received strength of a plurality of antennas is added.

FIG. 14 shows an antenna layout drawing 124' in which received strength information of respective antennas is displayed together with the layout drawing of the antennas. In the antenna layout drawing 124' shown in FIG. 14, the image display controller 115a displays antenna numbers and relative received strength of respective antenna numbers as character information, in addition to the display of the antenna layout drawing similar to the antenna layout drawing 124. In an example shown in FIG. 14, the image display controller 115a designates the received strength of antenna "3", which is the antenna having the largest received strength, as a reference, and displays the relative received strength of other antennas to the reference value of "100".

The image display controller 115a can also display the received strength itself of respective antennas, instead of the relative received strength. Further, the image display controller 115a can control the display such that at least one of the display tone, display chroma, and display brightness of respective antennas in the antenna layout drawing is made different corresponding to the received strength or the relative received strength and displayed, instead of displaying the received strength information of respective antennas as character information. In this case, for example, the display color of the antenna can be sequentially changed from red to blue, corresponding to the received strength.

Thus, since the image display controller 115a performs control so as to display the arrangement of respective antennas in correspondence with the received strength information, the observer and the like can estimate the imaging position of the images of the subject in more detail.

In the second embodiment, the series of images displayed by the image display apparatus 104 are explained as the series of images of the subject imaged by using the capsule endoscope 102 introduced into the subject 101, however, it is not necessarily interpreted by limiting to the images of the subject, and optional images taken at a plurality of points in time can be used, and an image pickup device and an imaging object can be optional.

Third Embodiment

Figure 15:
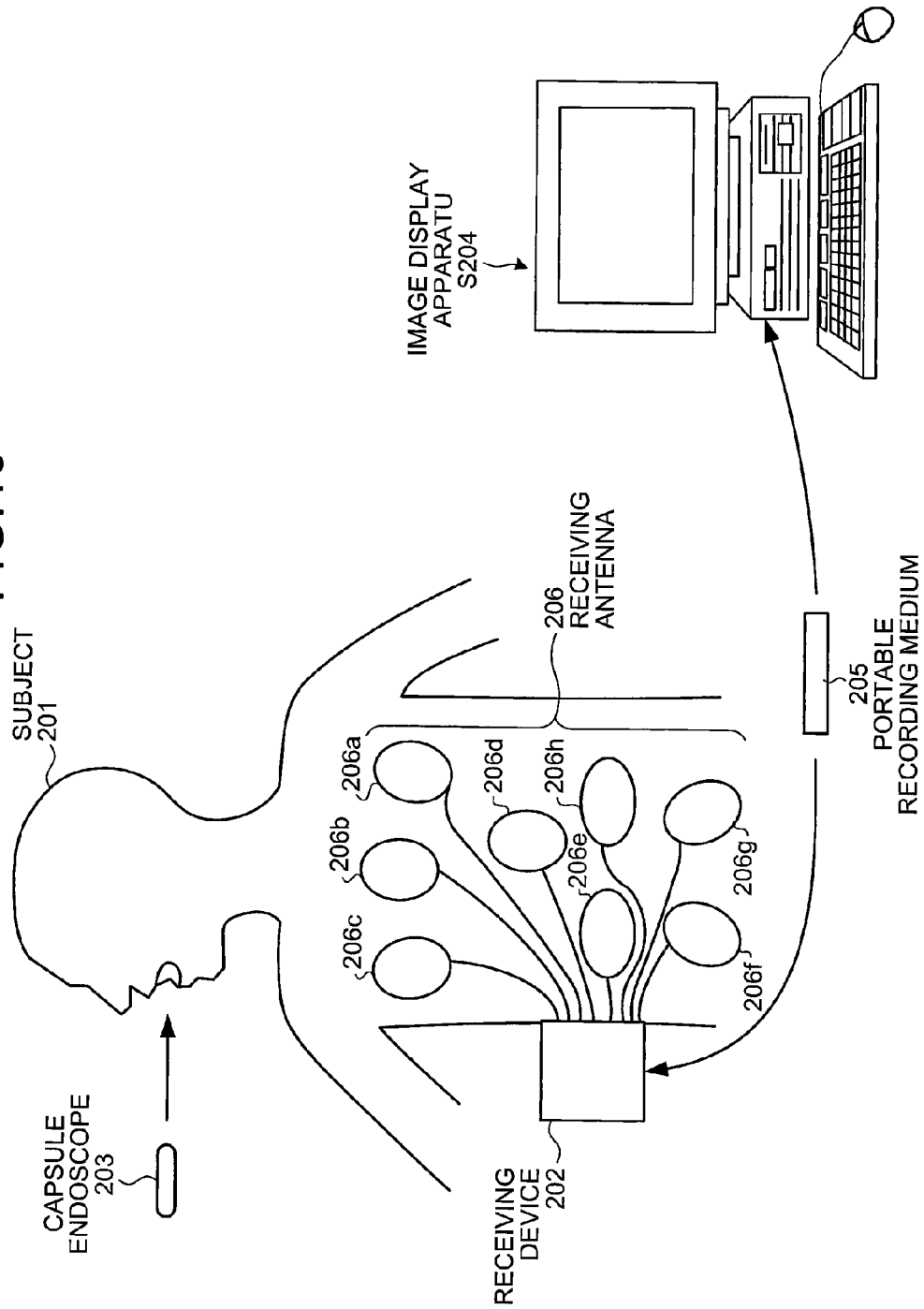
FIG. 15 is a schematic diagram of an overall configuration of a wireless intra-subject information acquiring system including a receiving device according to a third embodiment of the present invention.

A wireless intra-subject information acquiring system according to a third embodiment of the present invention is explained next. FIG. 15 is a schematic diagram of an overall configuration of the wireless intra-subject information acquiring system. The wireless intra-subject information acquiring system uses a capsule endoscope as an example of a body-insertable apparatus.

As shown in FIG. 15, the wireless intra-subject information acquiring system includes a capsule endoscope 203 that is introduced into a body of a subject 201 and wirelessly transmits image data of imaged subject image to a receiving device 202, the receiving device 202 that receives the image data wirelessly transmitted from the capsule endoscope 203, an image display apparatus 204 that displays the images of the subject based on a image signal received by the receiving device 202, and a portable recording medium 205 that transfers image data and the like between the receiving device 202 and the image display apparatus 204.

The receiving device 202 includes a receiving antenna 206, which includes a plurality of antennas 206a to 206h attached to the body surface of the subject 201. The receiving device 202 receives the image data wirelessly transmitted from the capsule endoscope 203 via the receiving antenna 206. The antennas 206a to 206h are achieved, for example, by using a loop antenna, and arranged at predetermined positions on the body surface of the subject 201, that is, at positions corresponding to respective internal organs inside the subject 201, which is a passage route of the capsule endoscope 202.

The antennas 206a to 206h can be arranged at predetermined positions on a jacket or the like worn by the subject 201. In this case, the antennas 206a to 206h are arranged at the predetermined positions on the body surface of the subject 201 via the jacket or the like. Arrangement of the antennas 206a to 206h can be optionally changed according to the purpose of observation and diagnosis of the inside of the subject 101. The number of antennas included in the receiving antenna 206 is not necessarily eight shown as the antennas 206a to 206h, and can be more or less than eight.

The image display apparatus 204 is achieved, for example, by a workstation including a CRT, a liquid crystal display or the like, and performs image display based on the image data acquired via the portable recording medium 205 or the like. The image display apparatus 204 can output image data to an output unit such as a printer and display the image data. The image display apparatus 204 can include a communication function with external devices, so as to acquire or output image data by wire communication or wireless communication.

The portable recording medium 205 is achieved by CompactFlash® Memory, CD, DVD, or the like, is detachable relative to the receiving device 202 and the image display apparatus 204, and can output or record various pieces of information such as image data when the portable recording medium 205 is set in the receiving device 202 or the image display apparatus 204. The portable recording medium 205 is set in the receiving device 202, for example, while the capsule endoscope 203 is introduced into the subject 201, and records the image data received by the receiving device 202 from the capsule endoscope 203. Further, after the capsule endoscope 203 is discharged from the subject 201, the portable recording medium 205 is taken out from the receiving device 202 and set in the image display apparatus 204, to output the recorded image data to the image display apparatus 204.

Thus, since transfer of image data between the receiving device 202 and the image display apparatus 204 is performed by the portable recording medium 205, the subject 201 can freely move while the capsule endoscope 203 is introduced therein. The transfer of data between the receiving device 202 and the image display apparatus 204 can be performed by wire communication or wireless communication.

Figure 16:
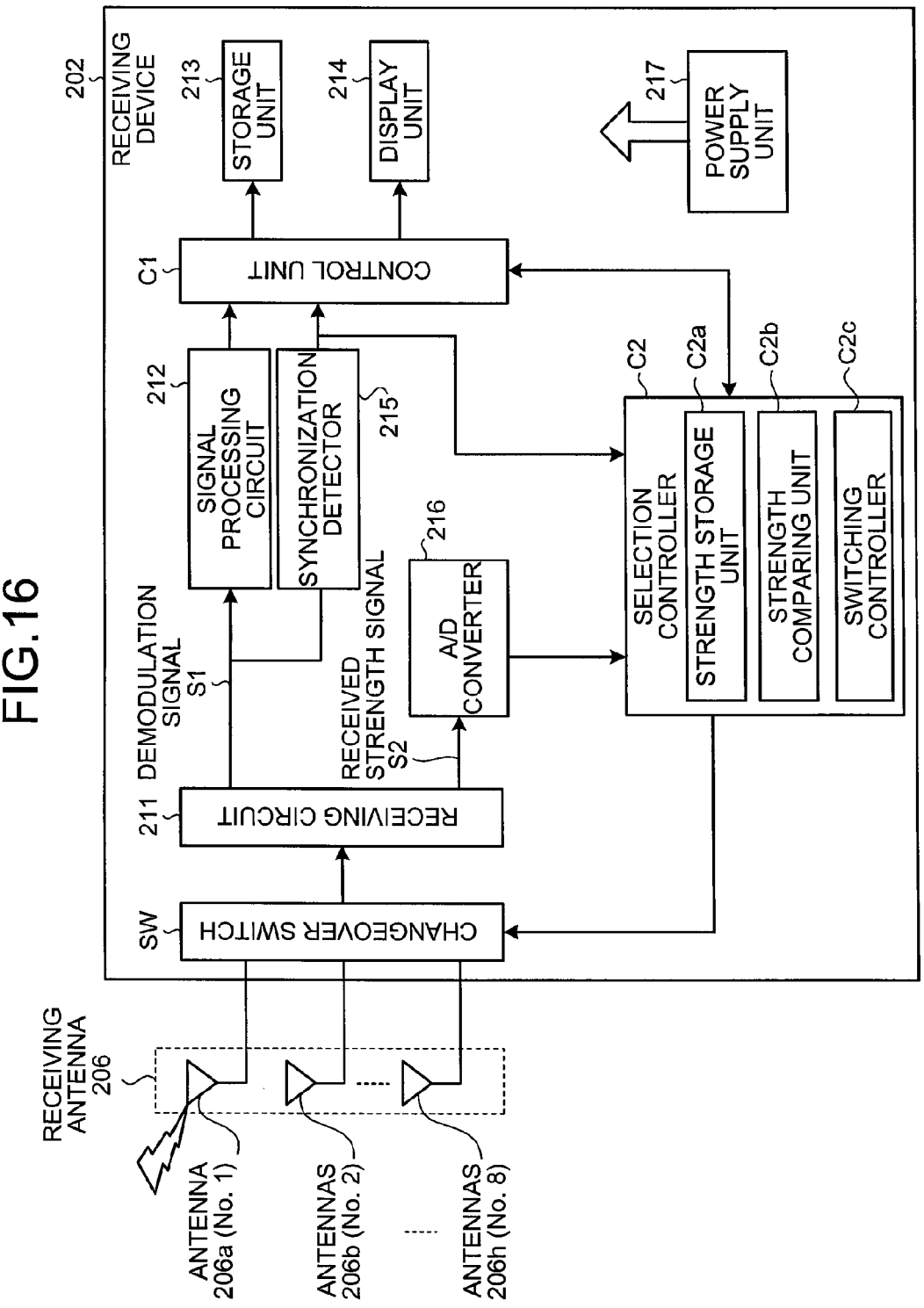
FIG. 16 is a block diagram of a configuration of the receiving device shown in FIG. 15.

The receiving device 202 is explained with reference to FIG. 16. FIG. 16 is a block diagram of a configuration of the receiving device 202. As shown in FIG. 16, the receiving device 202 has a function for performing processing of the radio signal transmitted from the capsule endoscope 203. Specifically, the receiving device 202 includes a changeover switch SW that switches connection of the antennas 206a to 206h having a series of antenna numbers, a receiving circuit 211 connected to a subsequent stage of the changeover switch SW for amplifying and demodulating the radio signal from the antennas 206a to 206h switched by the changeover switch SW, a signal processing circuit 212 connected at a subsequent stage of the receiving circuit 211, a synchronization detector 215, and an A/D converter 216.

A control unit C1 connects the signal processing circuit 212, the synchronization detector 215, the A/D converter 216, a storage unit 213 corresponding to the portable recording medium 205, a display unit 214, and a selection controller C2. The selection controller C2 includes a strength storage unit C2a, a strength comparing unit C2b, and switching controller C2c, gives a switching instruction of the changeover switch SW, and instructs a processing timing of the synchronization detector 215, the A/D converter 216, and the control unit C1. A power supply unit 217 supplies power to the respective units, and is achieved, for example, a battery.

The changeover switch SW selectively connects any one of the antennas 206a to 206h based on the switching instruction from the selection controller C2, and outputs the radio signal from the connected antenna 206a to 206h to the receiving circuit 211. The receiving circuit 211 amplifies the input radio signal, outputs a demodulated demodulation signal S1 to the signal processing circuit 212 and the synchronization detector 215, and outputs a received strength signal S2, which is received electric-field strength of the amplified radio signal, to the A/D converter 216.

The signal processing circuit 212 outputs the image data processed based on the demodulation signal S1 to the control unit C1, and the control unit C1 stores the image data in the storage unit 213, and allows the display unit 214 to display and output the image data. The synchronization detector 215 extracts synchronization information included in the demodulation signal S1 and outputs the synchronization information to the control unit C1 and the selection controller C2. The control unit C1 and the selection controller C2 execute various types of processing such as reception processing of the radio signal, designating the acquired synchronization information as a reference of the processing timing. The A/D converter 216 converts the input received strength signal S2 to a digital signal and outputs the digital signal to the selection controller C2.

The selection controller C2 refers to the synchronization information output from the synchronization detector 215, and upon reception of the synchronization information, the selection controller C2 continuously changes over the antennas 206a to 206h during a received strength measurement period of the radio signal, to measure the received electric-field strength of the respective antennas, so as to select and change over to the antenna having the largest received electric-field strength as the receiving antenna that receives the image signal.

On the other hand, when the synchronization information is not received, the selection controller C2 repeats an antenna switching process in which the antennas 206a to 206h are continuously switched to measure the received electric-field strength of each antenna in a cycle shorter than a total period of the received strength measurement period and a image signal period, which is the transmission period of the transmission information held by the radio signal, for recovering synchronization with the radio signal, to detect the antenna having the largest received electric-field strength. The selection controller C2 selects and switches the detected antenna having the largest strength as the receiving antenna for receiving the synchronization information, and continues to connect the antenna until at least the synchronization signal is received. The selection controller C2 can perform control such that the antenna switching process for detecting the antenna having the largest strength is repeated for a longer period than a non-transmission period acquired by subtracting the transmission period of the transmission information from the transmission cycle of the radio signal.

Figure 17:
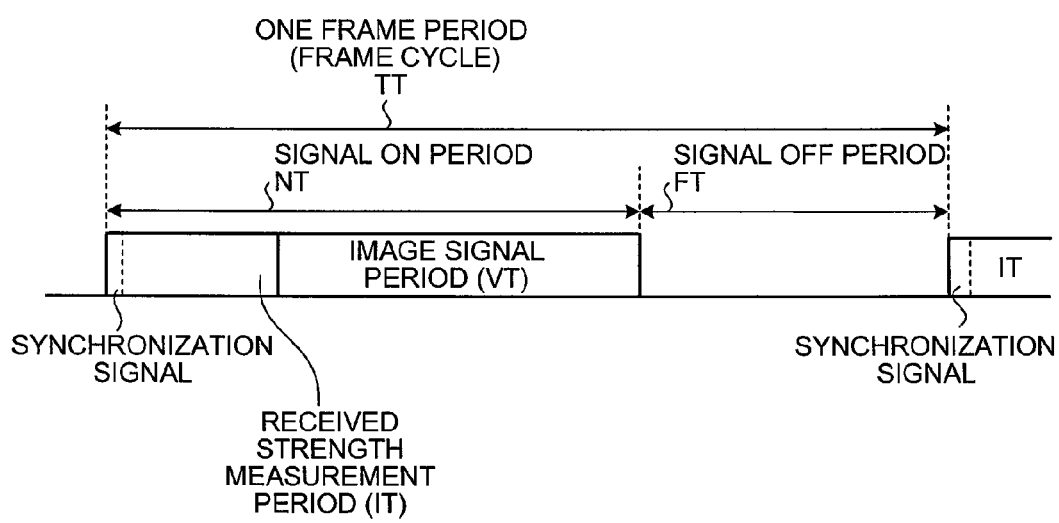
FIG. 17 shows a frame format of a radio signal transmitted from a capsule endoscope shown in FIG. 15.

The outline of the antenna switching process controlled by the selection controller C2 is explained more specifically with reference to FIGS. 17 to 20. The radio signal transmitted from the capsule endoscope 203 is explained first. As shown in FIG. 17, in the radio signal transmitted from the capsule endoscope 203, the transmission information is transmitted in a unit of frame, and the frame is formed of the received strength measurement period (IT) and the image signal period (VT). The received-strength measurement period corresponds to a preamble signal period for reception adjustment, and the synchronization signal indicating the transmission timing from the capsule endoscope capsule endoscope 203 is included in the head of the period. The image signal period can include a control signal necessary for receiving the image signal in addition to the image signal itself.

Each frame can include a non-signal state between respective frames, or respective frames can be transmitted continuously. In other words, a signal OFF period FT as a non-transmission period acquired by subtracting a signal ON period NT as a transmission period of the transmission information for each frame from a frame cycle TT of frame transmission is set to a predetermined period more than 0 corresponding to the type of the transmitted radio signal. Further, the length of the frame cycle TT is flexibly adjusted such that it is set short in an observable imaging region and a region in which the movement of the capsule endoscope 203 is fast, from a standpoint of effective use of the battery of the capsule endoscope 203.

Figure 18:
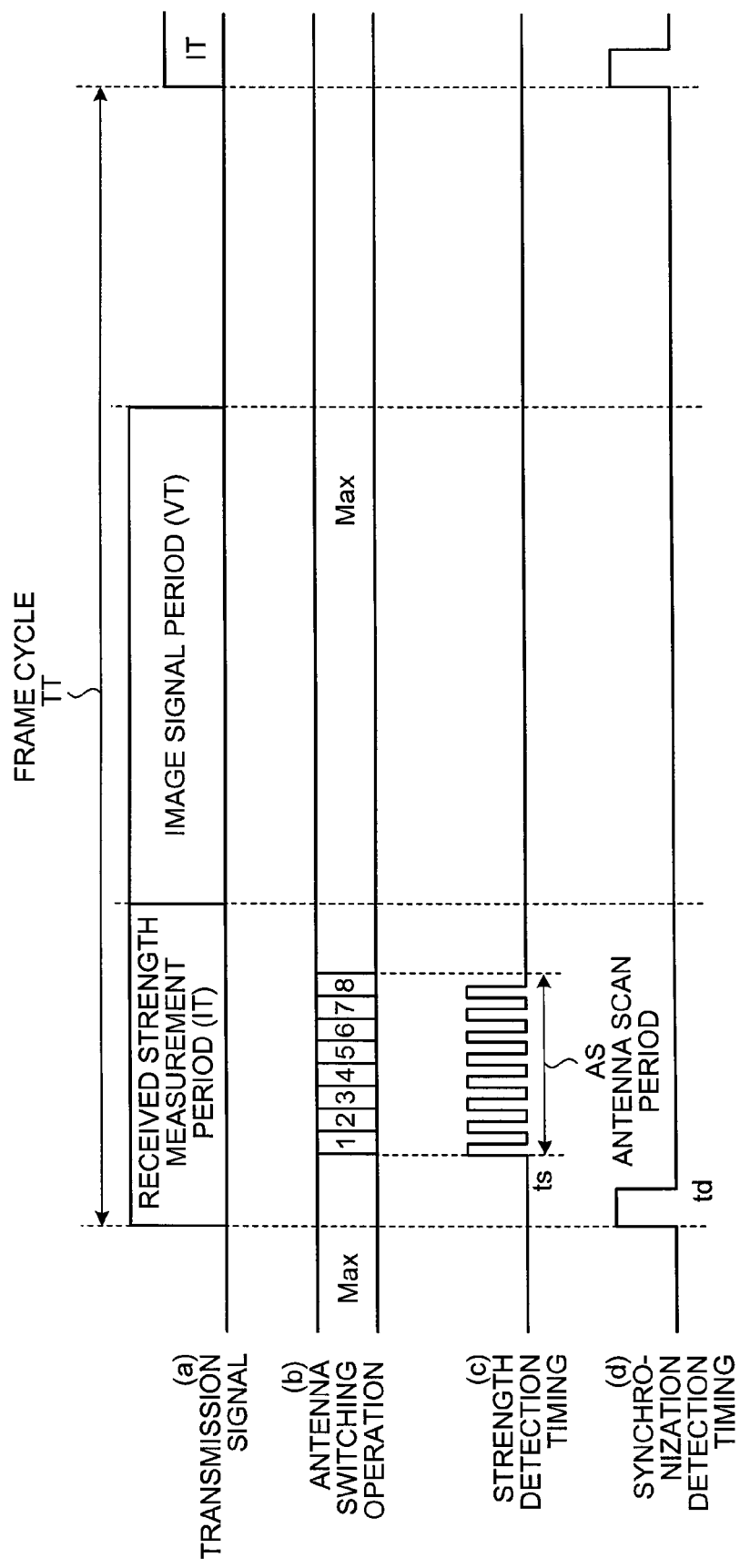
FIG. 18 is a time chart of an antenna switching process when a synchronization signal is received.

The normal-antenna switching process performed when the synchronization signal is received is explained with reference to a time chart shown in FIG. 18. As shown in FIG. 18, at a timing td in the received strength measurement period, the synchronization signal is received by the pre-selected and switched antenna. When the synchronization information is detected by the synchronization detector 215, the selection controller C2 instructs the changeover switch SW to execute an antenna scan process as the antenna switching process for continuously switching the antennas 206a to 206h in the timing td in the same received strength measurement period.

In the antenna scan process, the selection controller C2 measures the received electric-field strength (hereinafter, "received strength") of the respective antennas 206a to 206h, detects the antenna having the largest received strength, selects the detected antenna as the receiving antenna in the image signal period, and instructs the changeover switch SW to switch the antenna. For example, the selection controller C2 sequentially switches the antennas, as shown in FIG. 18, in order of antenna number No. 1 to No. 8 corresponding to the antennas 206a to 206h, detects the antenna (Max) having the largest received strength, and switches to the detected antenna (Max) after the antenna scan process. The selection controller C2 executes the antenna scan process in a predetermined antenna scan period AS shorter than the received strength measurement period.

Thus, the selection controller C2 can make the antenna having the largest received strength receive the image signal for each image signal period by performing the antenna scan process for each received strength measurement period, and selecting and switching the antenna (Max) having the largest received strength.

The antenna switching process for recovering synchronization performed when the synchronization signal is not received is explained. For example, as shown in FIG. 19, when each synchronization detection timing in the receiving device 202 is a timing $td_n$ and a timing $td_{n+1}$, and not the timing capable of detecting the synchronization signal in each received strength detection period (IT) with respect to the transmission signal in which the n-th frame (n) and the (n+1)th frame (n+1) are sequentially transmitted, the signal transmitted during the received strength measurement period may not be received during the antenna scan period AS with the normal-antenna switching process.

Figure 19:
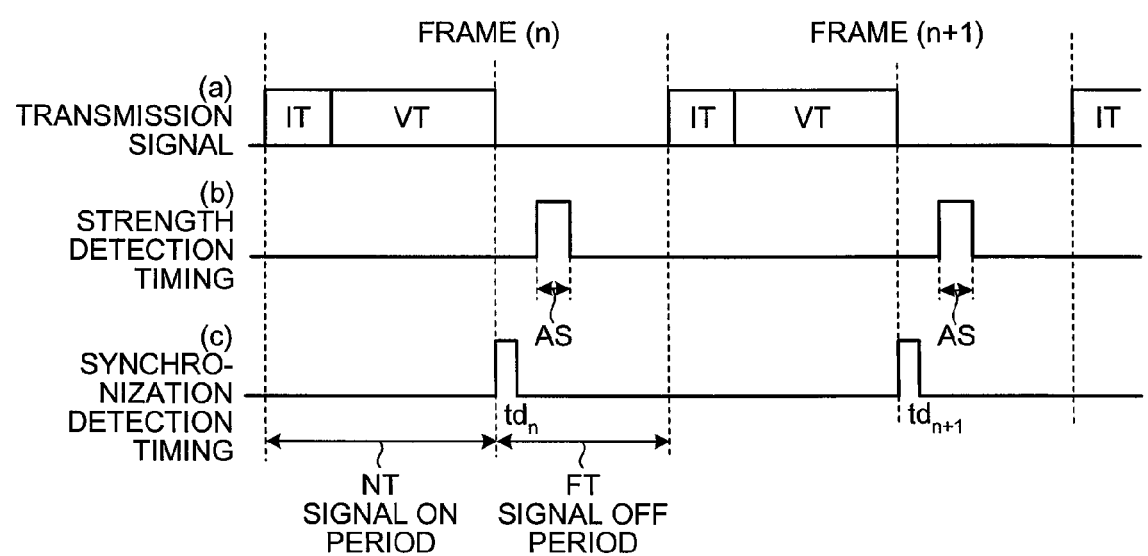
FIG. 19 is a time chart of a signal detection timing when the synchronization signal is not received.

Further, in the case shown in FIG. 19, since the respective antenna scan periods AS are included in the signal OFF period, the reception signal cannot be acquired from any antenna switched by the antenna scan process, and it cannot be determined which antenna of the antennas 206a to 206h is at a position capable of receiving the transmission signal. During a period in which synchronization with the transmission signal cannot be achieved (asynchronization period), respective strength detection timing is determined based on an internal clock of the receiving device 202.

Figure 20:
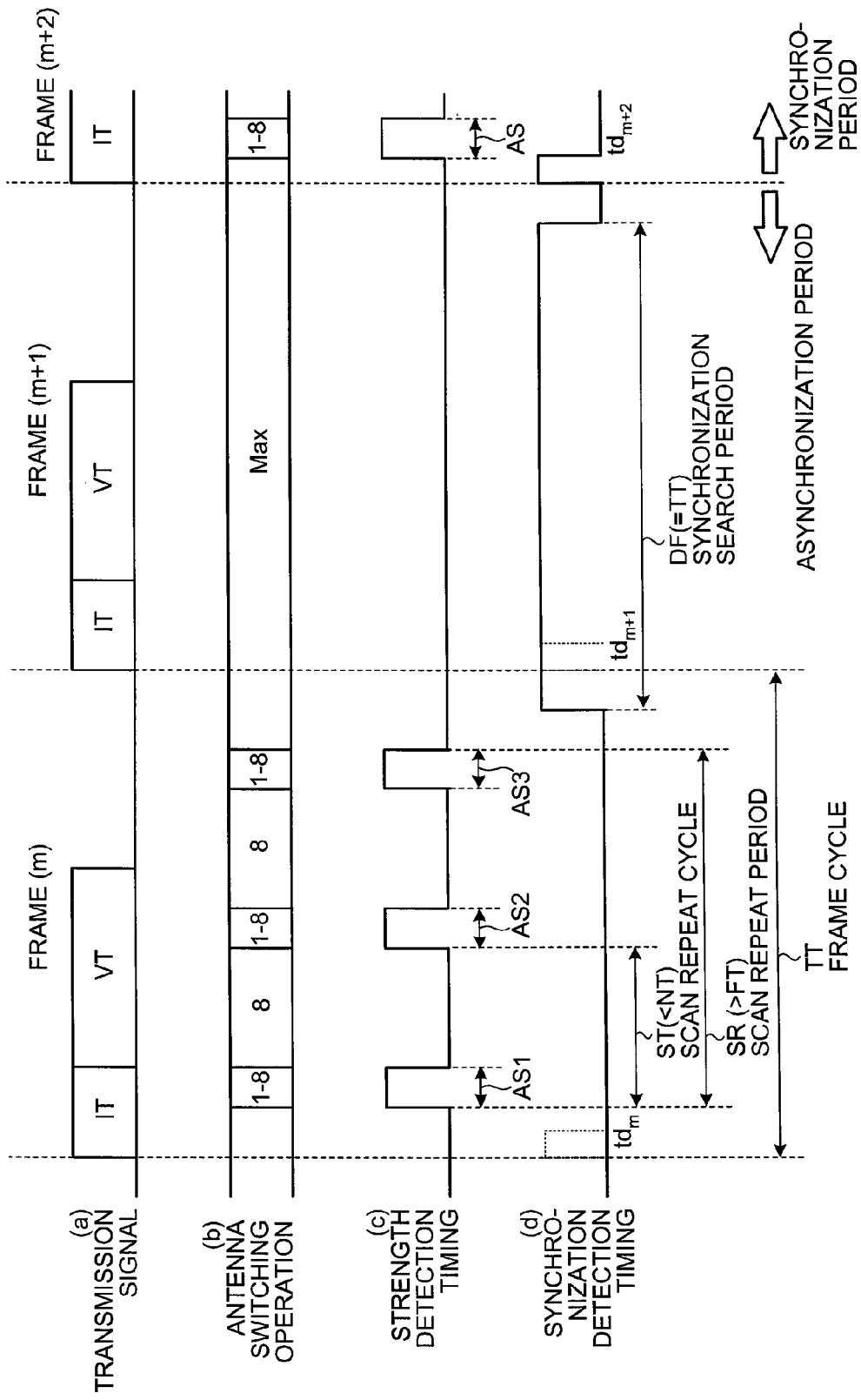
FIG. 20 is a time chart of the antenna switching process when the synchronization signal is not received.

The selection controller C2 performs the antenna switching process as shown in FIG. 20 for recovering synchronization from the asynchronization state. That is, when the synchronization signal is not received by the pre-selected antenna, for example, the synchronization signal of a frame (m) is not received at a timing $td_m$ shown in FIG. 20, the selection controller C2 controls the changeover switch SW to execute a scan repeat process for repeating the antenna scan process in a scan repeat cycle ST shorter than the signal ON period NT. The selection controller C2 further controls so as to execute the scan repeat process only in a scan repeat period SR longer than the signal OFF period FT. In an example shown in FIG. 20, the antenna scan process is repeated three times corresponding to the antenna scan periods AS1 to AS3 for each scan repeat cycle ST in the scan repeat period SR.

Thus, the selection controller C2 can perform at least one antenna scan process during the signal ON period by performing the scan repeat process. The respective received strength of the antennas 206a to 206h can be reliably measured, by the antenna scan process performed during the signal ON period, and the antenna at a position capable of receiving the transmission signal can be detected, and the antenna having the largest strength can be detected. In the example shown in FIG. 20, the antenna scan periods AS1 and AS2 are included in the signal ON period of the frame (m), and the antenna having the largest strength can be detected by the antenna scan process in the respective antenna scan periods AS1 and AS2.

After detecting the antenna having the largest strength by the scan repeat process, the selection controller C2 selects and switches the detected antenna having the largest strength as the receiving antenna for receiving the synchronization signal, to perform a synchronization search process for searching the synchronization signal. That is, the selection controller C2 continuously receives the transmission signal by the switched antenna (Max) having the largest strength, monitors the output from the synchronization detector 215, and detects the synchronization information. At this time, the selection controller C2 can reliably detect the synchronization information by continuously receiving the transmission signal only for a synchronization search period DF substantially equal to the frame cycle TT. In the example shown in FIG. 20, the selection controller C2 can detect the synchronization information by receiving the synchronization signal of a frame (m+1) at a timing $td_{m+1}$.

The selection controller C2 can promptly and reliably recover synchronization from the point in time at which the synchronization signal was not received by executing the scan repeat process and the synchronization search process. In the example shown in FIG. 20, synchronization can be recovered in two frame periods of frame (m) and frame (m+1) since the synchronization signal was not received, and the synchronization signal can be received at a timing $td_{m+2}$ after the frame (m+2). Therefore, the selection controller C2 can shift to the normal-antenna switching process shown in FIG. 18.

It has been explained that the scan repeat process is continued during the predetermined scan repeat period SR. However, the selection controller C2 can finish the scan repeat process and start the synchronization search process at a point in time when the antenna having the largest strength can be detected, that is, when the received strength of the antennas 206a to 206h can be reliably measured. In the synchronization search process, the selection controller C2 can finish the synchronization search process when the synchronization signal is received by the antenna having the largest strength and the synchronization information can be detected. In other words, the selection controller C2 can control so as to continue to connect the antenna having the largest strength until at least the synchronization signal is received, after the antenna having the largest strength is connected for the synchronization search process.

Figure 21:
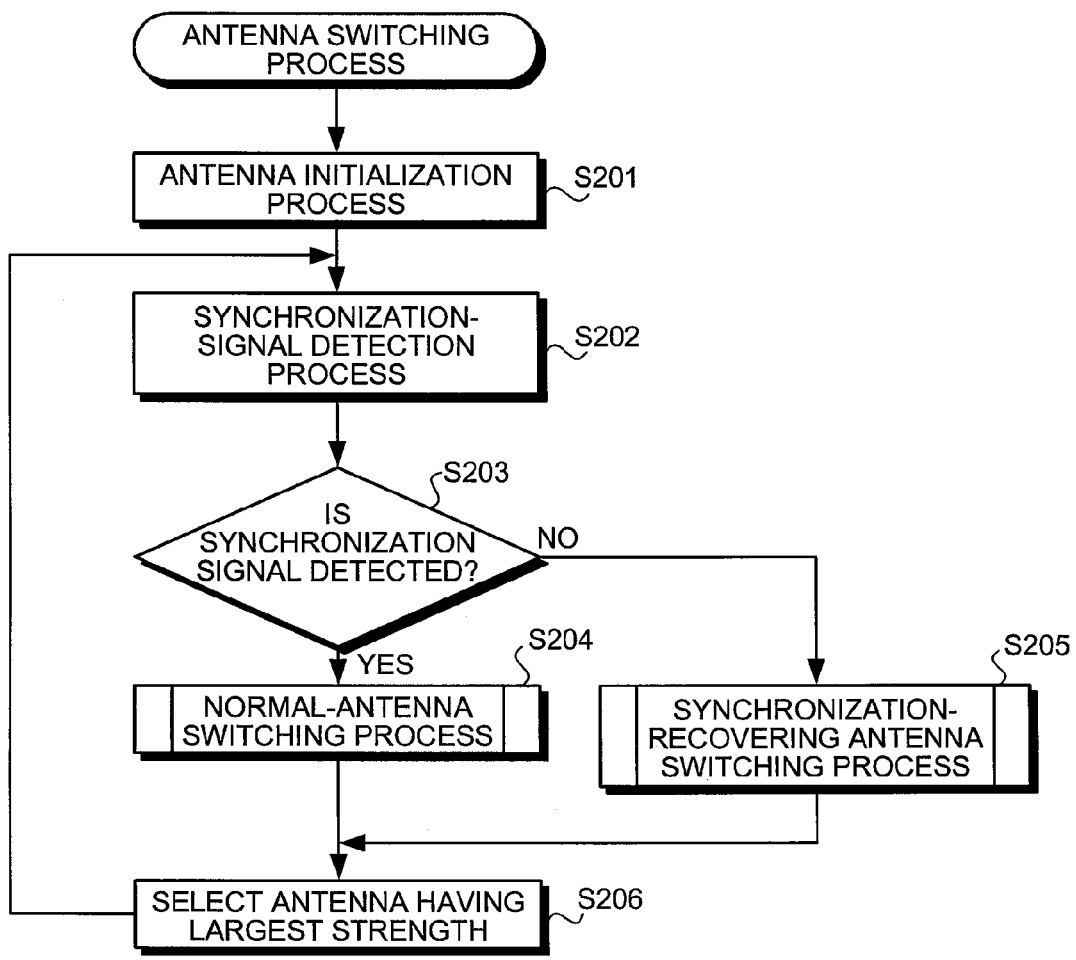
FIG. 21 is a flowchart of an antenna switching process procedure performed by the receiving device shown in FIG. 15.

A process procedure of the antenna switching process performed by the receiving device 202 is explained with reference to a flowchart shown in FIG. 21. The antenna switching process is controlled and executed by the selection controller C2. As shown in FIG. 21, the selection controller C2 performs an antenna initialization process in which the antenna to receive the synchronization signal first is selected and connected (step S201). At step S201, the selection controller C2 selects and connects, for example, antenna number No. 1 as the receiving antenna. The settable antenna numbers No. 1 to No. 8, respectively correspond to the antennas 206a to 206h as shown in FIG. 16.

The selection controller C2 performs a synchronization signal-detection process for detecting the synchronization signal from the transmission signal at the head of the frame (step S202), and determines whether the synchronization signal is detected (step S203). When the synchronization is detected (step S203: Yes), the selection controller C2 executes the normal-antenna switching process shown in FIG. 18 (step S204). When the synchronization signal is not detected (step S203: No), the selection controller C2 executes synchronization-recovering-antenna switching process shown in FIG. 20 (step S205). After steps S204 or S205, the selection controller C2 selects and connects the antenna having the largest strength (step S206). Thereafter, the selection controller C2 repetitively executes the processing from step S202 until an instruction to finish the predetermined process is received.

Figure 22:
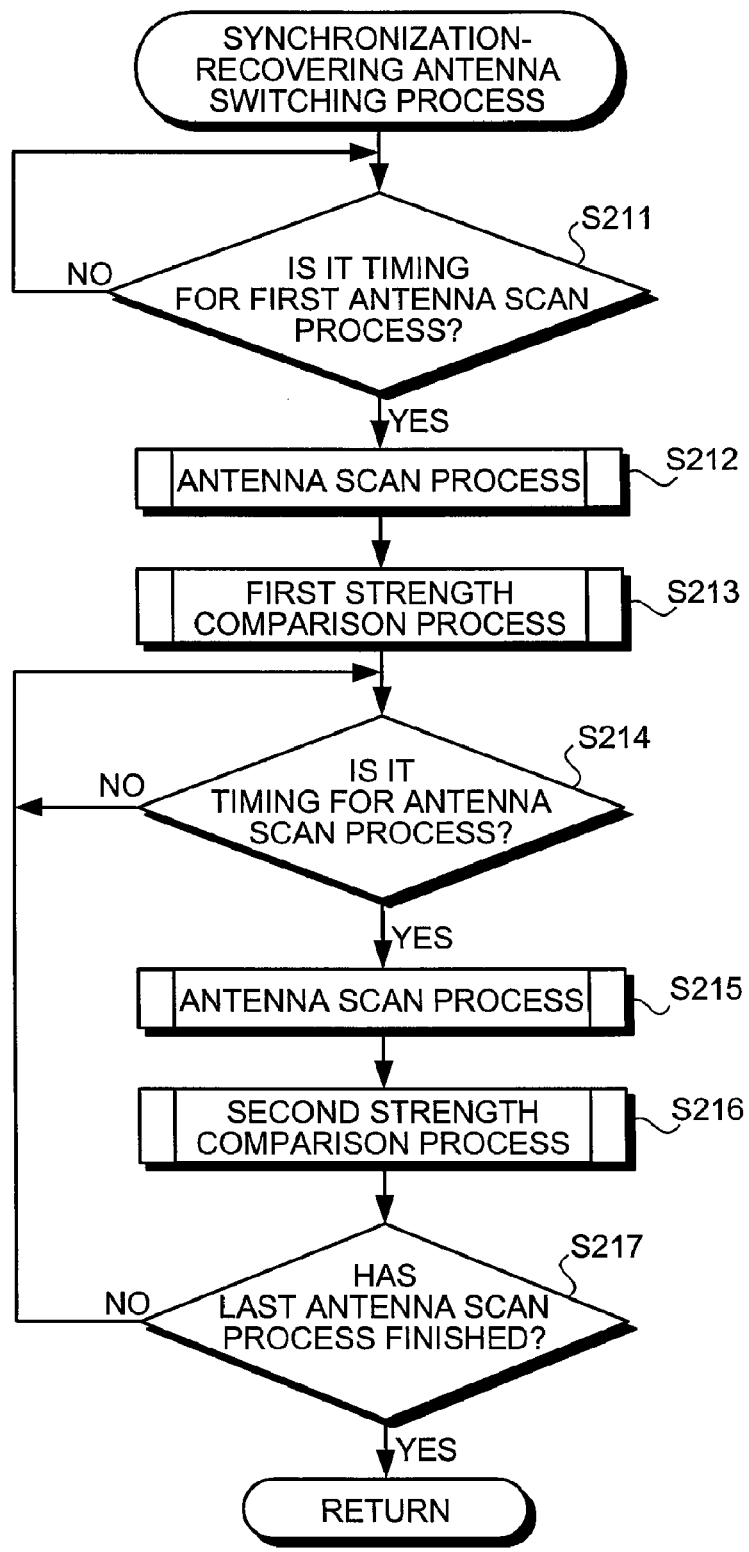
FIG. 22 is a flowchart of a synchronization-recovering-antenna switching process procedure shown in FIG. 21.

The synchronization-recovering-antenna switching process procedure at step S205 is explained with reference to a flowchart shown in FIG. 22. As shown in FIG. 22, the selection controller C2 determines whether it is a timing for the first antenna scan process in the scan repeat process based on the internal clock (step S211) as a reference, and when it is not the timing for the antenna scan process (step S211: No), the selection controller C2 repeats the determination process and waits until the predetermined timing.

When it is the timing for the antenna scan process (step S211: Yes), the selection controller C2 sequentially switches the antennas 206a to 206h in order of, for example, a series of antenna numbers, to perform the antenna scan process for recording the received strength of the respective antennas (step S212), and executes a first strength-comparison process for recording the information of the antenna having the largest strength by comparing the received strength of the respective antennas as the scan process result (step S213).

The selection controller C2 determines whether it is a timing for the second antenna scan process in the scan repeat process, that is, whether it is a point in time when the predetermined scan repeat cycle ST has passed since the start of the antenna scan process immediately before (step S214), and when it is not the timing for the antenna scan process (step S214: No), the selection controller C2 repeats the determination process, and waits until the predetermined timing. When it is the timing for the antenna scan process (step S214: Yes), the selection controller C2 performs the antenna scan process (step S215), to execute a second strength-comparison process for updating and recording the information of the antenna having the largest strength by comparing the received strength of the respective antennas as the antenna scan process result (step S216).

Subsequently, the selection controller C2 determines whether the predetermined last antenna scan process in the scan repeat process has finished (step S217). When the last antenna scan process has not finished (step S217: No), the selection controller C2 repeats the processing from step S214, and when the last antenna scan process has finished (step S217: Yes), the selection controller C2 returns to step S205.

Figure 23:
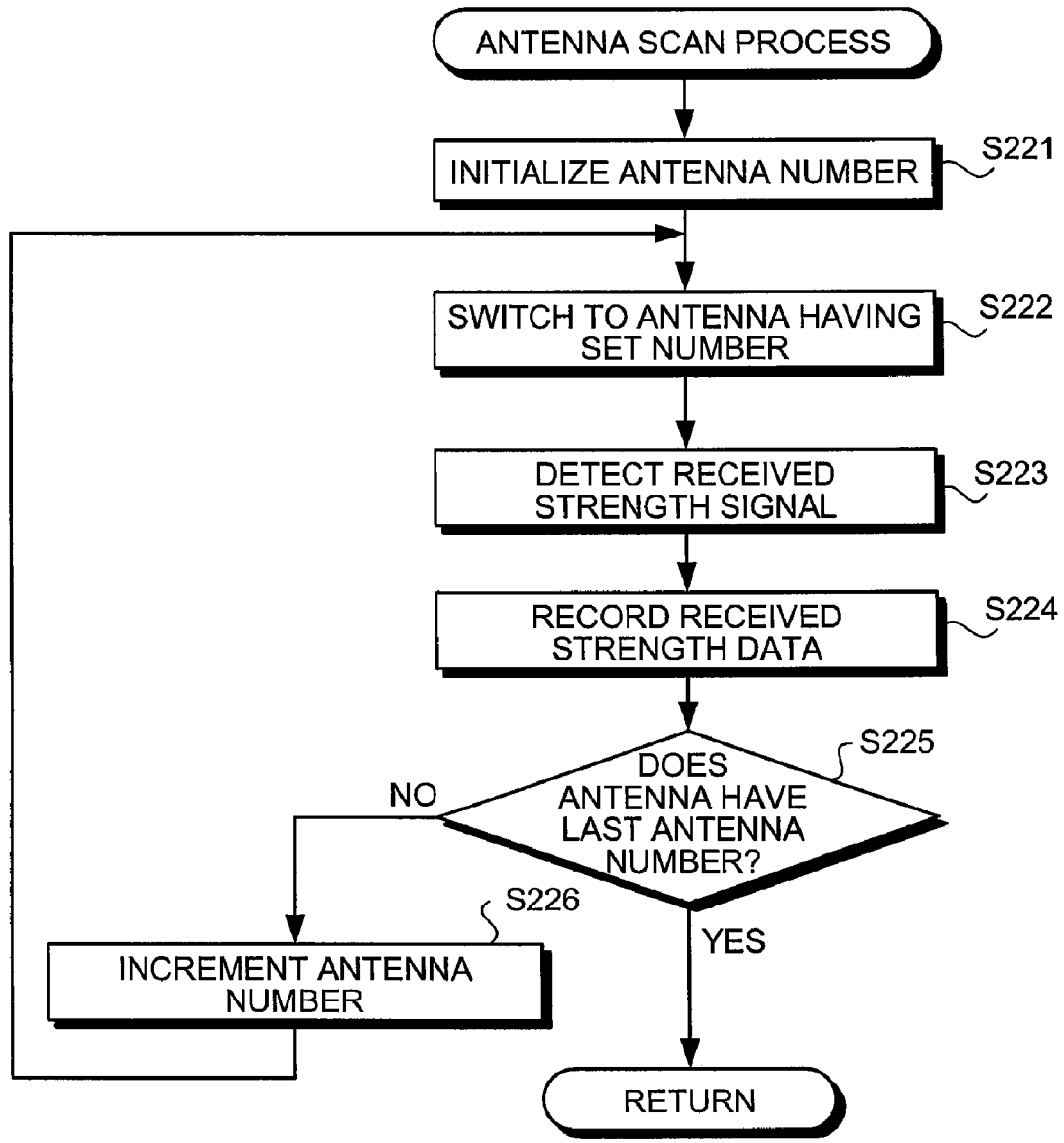
FIG. 23 is a flowchart of an antenna scan process procedure shown in FIG. 22.

An antenna scan process procedure from steps S212 and S215 is explained with reference to a flowchart shown in FIG. 23. As shown in FIG. 23, the switching controller C2c included in the selection controller C2 initializes the antenna number of the antenna to receive the signal first in the antenna scan process (step S221). The switching controller C2c selects and sets, for example, antenna number No. 1 at step S221.

The switching controller C2c then switches the connection to the antenna having the antenna number set at step S221 (step S222), detects the received strength signal via the A/D converter 216 (step S223), and records the detected received strength data in the strength storage unit C2a (step S224). The switching controller C2c records the received strength data in association with the received antenna number at step S224.

The switching controller C2c determines whether the connected antenna has the last antenna number, for example, antenna number No. 8 in the antenna scan process (step S225). When the antenna does not have the last number (step S225: No), the switching controller C2c increments the antenna number (step S226), to repeat the processing from step S222, and when the antenna has the last number (step S225: Yes), the switching controller C2c returns to the original process step, that is, steps S212 or S215.

Figure 24:
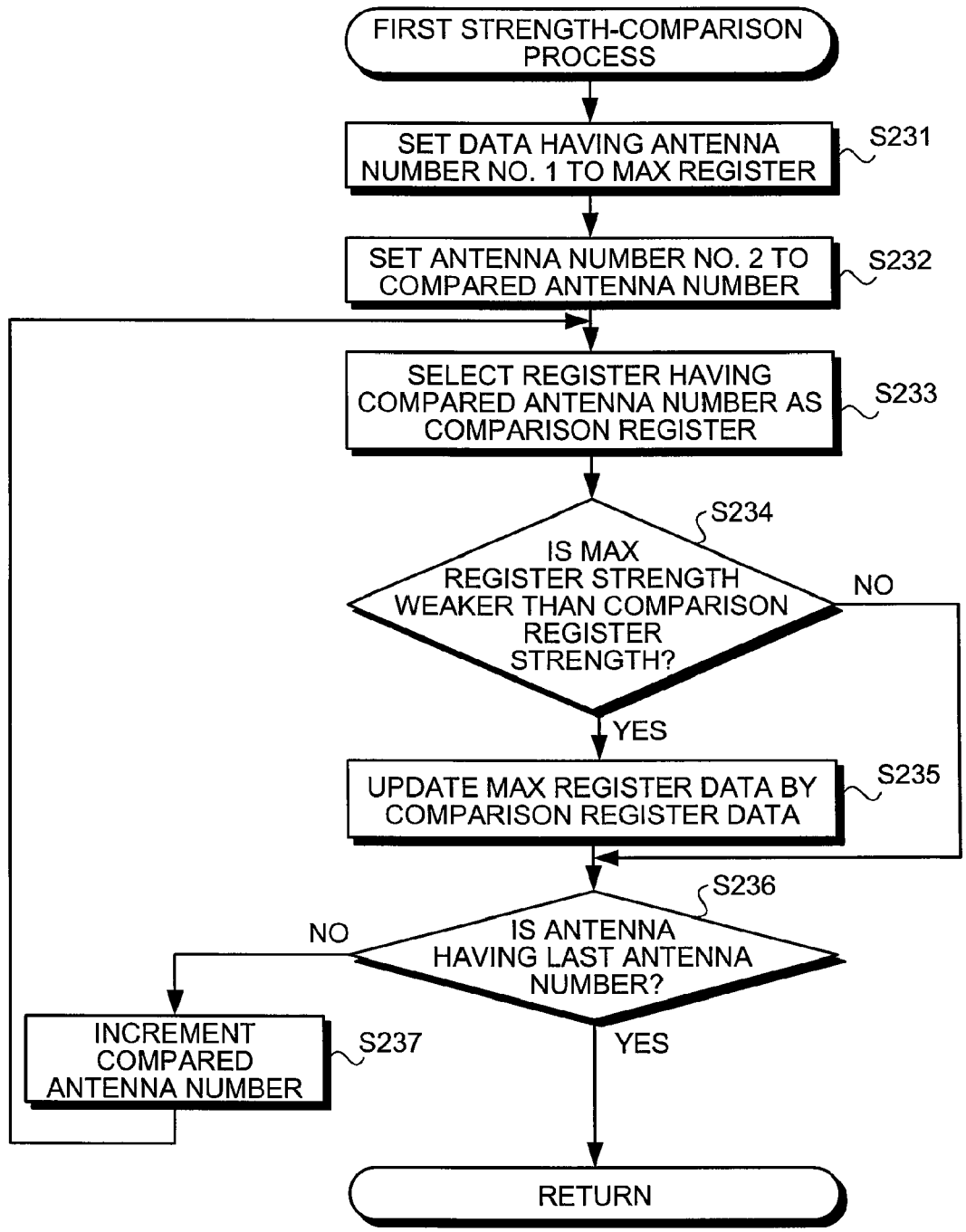
FIG. 24 is a flowchart of a first strength comparison process procedure shown in FIG. 22.

A first strength-comparison process procedure in step S213 is explained with reference to a flowchart shown in FIG. 24. As shown in FIG. 24, the strength comparing unit C2b of the selection controller C2 refers to the received strength data recorded in the strength storage unit C2a, and temporarily sets the received strength data of the antenna number No. 1 acquired by the first antenna scan process in a Max register corresponding to the antenna having the largest strength in the strength storage unit C2a (step S231). Further, the strength comparing unit C2b sets the antenna number No. 2 as a compared antenna number indicating the antenna, of which received strength data is compared with the temporary antenna having the largest strength (step S232).

The strength comparing unit C2b selects a register corresponding to the compared antenna number in the strength storage unit C2a as a comparison register (step S233), and determines whether the received strength recorded in the Max register (Max register strength) is smaller than the received strength recorded in the comparison register (comparison register strength) (step S234). When the Max register strength is smaller than the comparison register strength (step S234: Yes), the strength comparing unit C2b updates the data in the Max register by the data in the comparison register (step S235), and determines whether the compared antenna number corresponding to the comparison register is the last number in a series of antenna numbers, for example, antenna number No. 8 (step S236). On the other hand, when the Max register strength is not smaller than the comparison register strength (step S234: No), the strength comparing unit C2b proceeds to step S236.

When it is determined that the compared antenna number is not the last antenna number (step S236: No), the strength comparing unit C2b increments the compared antenna number (step S237), and repeats processing from step S233. When it is determined that the compared antenna number is the last antenna number (step S236: Yes), the strength comparing unit C2b returns to step S213.

Figure 25:
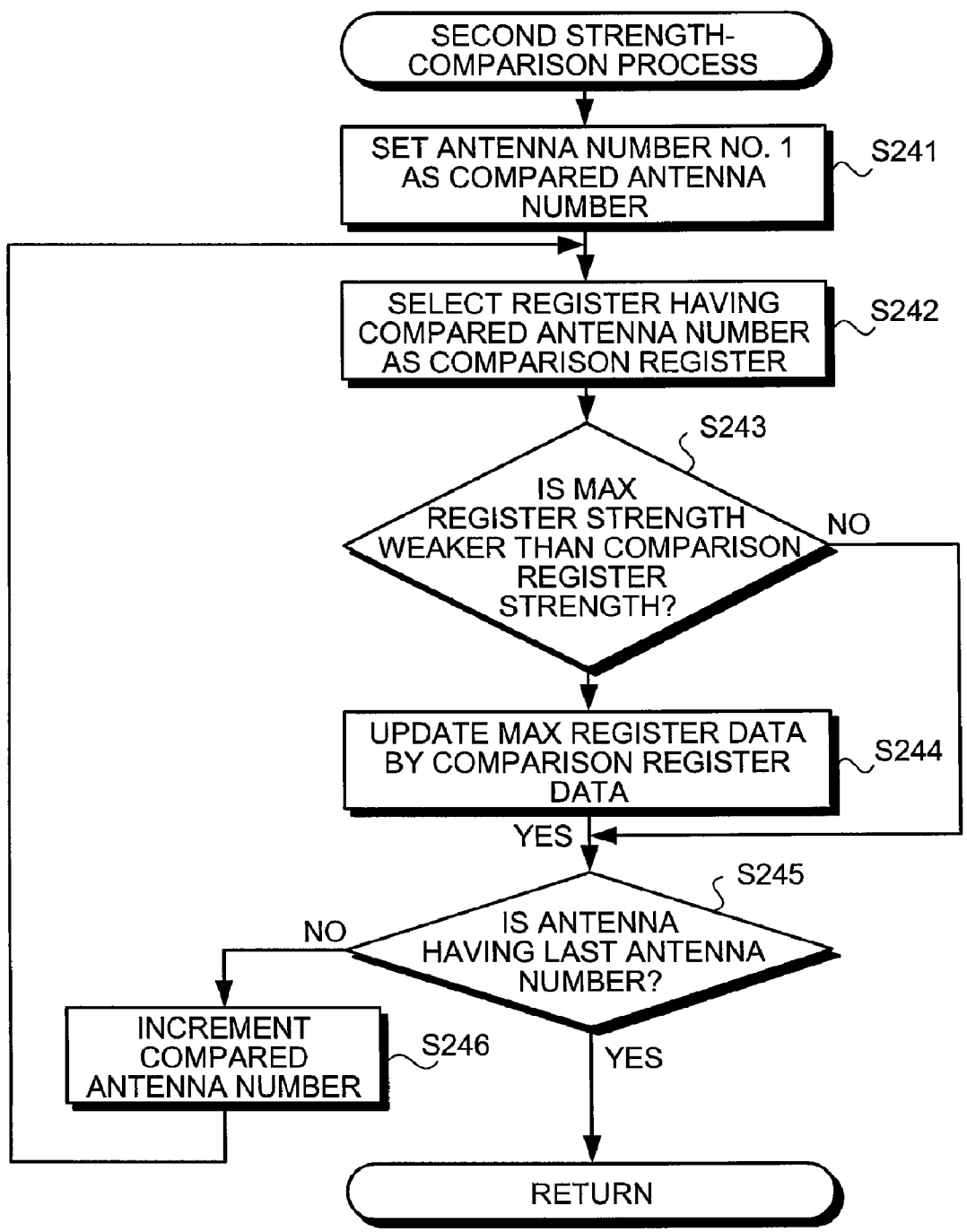
FIG. 25 is a flowchart of a second strength comparison process procedure shown in FIG. 22.

A second strength-comparison process procedure at step S216 is explained with reference to a flowchart shown in FIG. 25. In the second strength-comparison process, as is clear in comparison between the flowcharts shown in FIGS. 25 and 24, after antenna No. 1 is set as the compared antenna number (step S241), the same processing as at steps S233 to S237 in the first strength-comparison process is executed at steps S242 to 246. As the data in the Max register to be compared first in the second strength-comparison process, the data in the Max register at the time of finishing the first strength-comparison process is used.

Thus, in the synchronization-recovering-antenna switching process, the received strength of respective antennas in the respective antenna scan processes is sequentially compared in the first and the second strength-comparison processes, and the antenna number having the largest received strength is registered in the Max register, and the antenna of the antenna number registered in the Max register is finally detected as the antenna having the largest strength.

More specifically, for example, when the received strength data as shown in FIG. 26 is recorded, in the first strength-comparison process corresponding to the first antenna scan period AS1, the received strength of the antenna numbers No. 1 to No. 8 are sequentially compared, and lastly, the received strength "80" of the antenna number No. 1 is recorded in the Max register. In the second strength-comparison process corresponding to the second antenna scan period AS2, the received strength of the antenna numbers No. 1 to No. 8 are sequentially compared based on the Max register lastly recorded in the first antenna scan period AS1, and as a result, the data of the reference Max register, that is, the received strength "80" of the antenna number No. 1 is recorded as the last Max register as it is.

In the second strength-comparison process corresponding to the last (the third) antenna scan period AS3, as in the second antenna scan period AS2, the received strength of the antenna numbers No. 1 to No. 8 are sequentially compared based on the Max register lastly recorded in the second antenna scan period AS2, and as a result, the data of the reference Max register, that is, the received strength "80" of the antenna number No. 1 is recorded as the last Max register as it is. The antenna 206a corresponding to the antenna number No. 1 recorded in the last Max register is then detected as the antenna having the largest strength.

In the antenna scan process and the first and the second strength-comparison processes, the antenna number is switched in order of the number from No. 1. However, there is no limitation thereto, and for example, the antenna numbers can be sequentially switched at random without any duplication.

Further, the normal-antenna switching process at step S204 in the antenna switching process shown in FIG. 21 is achieved by the same process as the first antenna switching process in the synchronization-recovering-antenna switching process shown in FIG. 22, that is, the antenna scan process at step S212 and the first strength-comparison process at step S213.

In the receiving device 202 according to the third embodiment, when the synchronization signal has not been received by the pre-selected antenna, the selection controller C2 repeats the antenna switching process for measuring the received strength of respective antennas by continuously switching the antennas 206a to 206h, at a cycle shorter than the signal ON period NT, which is the transmission period of the transmission information included in the radio signal, and controls selection and switching of the antenna having the largest strength as the receiving antenna for receiving the synchronization signal. Accordingly, synchronization can be recovered quickly and reliably from the point in time when the synchronization signal was not received. Further, if the selection controller C2 performs control such that the antenna switching process for detecting the antenna having the largest strength is repeated for a longer period than the signal OFF period FT, which is the non-transmission period acquired by subtracting the transmission period of the transmission information from the transmission cycle of the radio signal, synchronization can be recovered more quickly and reliably. Accordingly, certainty and reliability of the receiving operation in the receiving device 202 can be further improved.

Modification

A modification of the third embodiment is explained. In the third embodiment, the selection controller C2 intermittently repeats the antenna scan process in the predetermined scan repeat cycle ST when the synchronization signal is not received. In this modification, however, the selection controller C2 controls so as to continuously repeat the antenna scan process.

Figure 27:
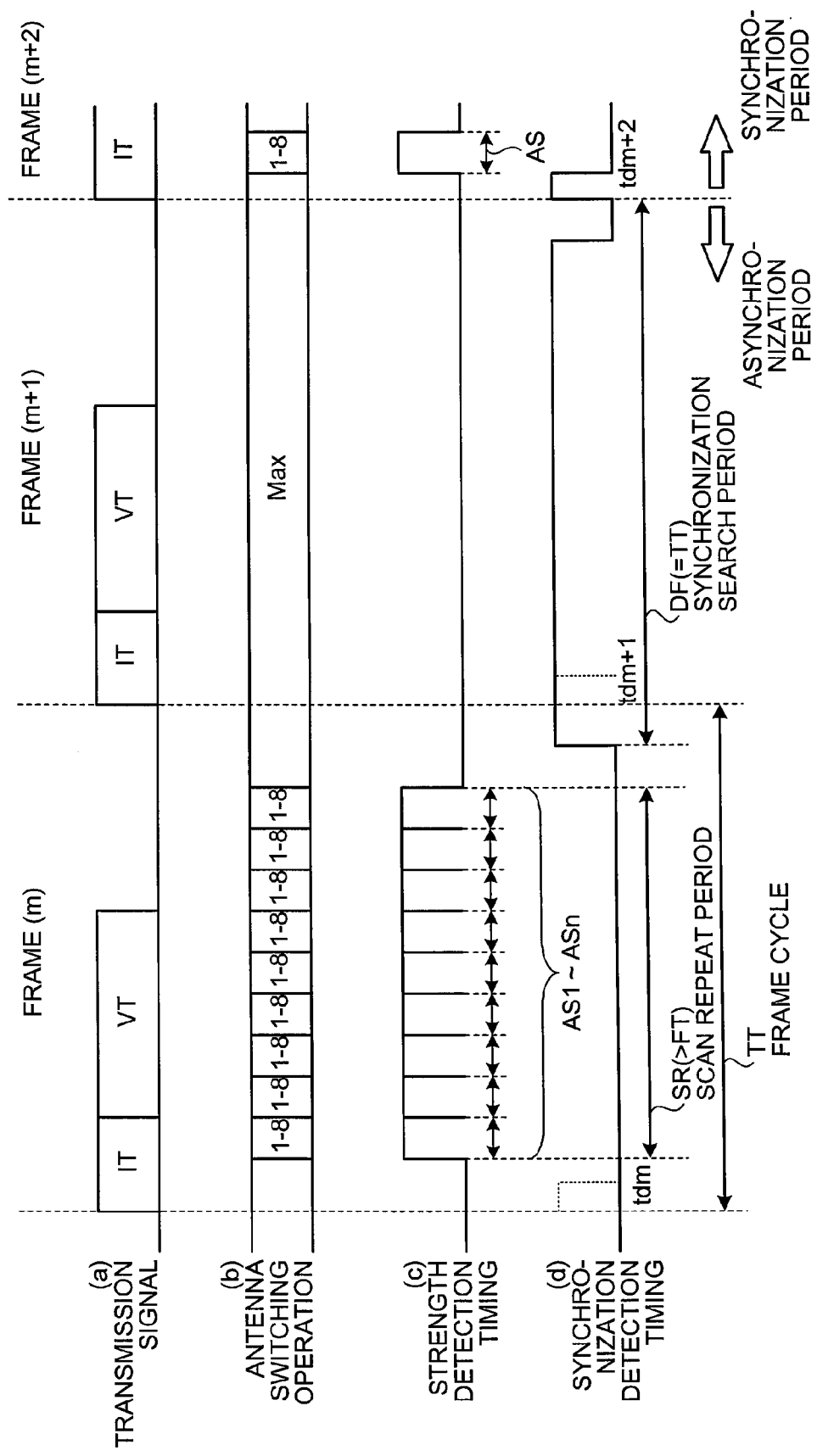
FIG. 27 is a time chart of the antenna switching process as a modification example when the synchronization signal is not received.

FIG. 27 is a time chart of the antenna switching process executed by the selection controller C2 when the synchronization signal is not received, in the modification. As shown in FIG. 27, the selection controller C2 controls the changeover switch SW so as to execute the scan repeat process in which the antenna scan process is continuously repeated, when the synchronization signal is not received by the pre-selected antenna, for example, when the synchronization signal of the frame (m) is not received at the timing $td_m$.

The selection controller C2 controls so as to execute the scan repeat process only in the scan repeat period SR longer than the signal OFF period FT. In an example shown in FIG. 27, the antenna scan process is continuously repeated n times corresponding to the antenna scan periods AS1 to AS3 during the scan repeat period SR. The scan repeat process according to the modification corresponds to a state where the scan repeat cycle ST of the scan repeat process according to the above embodiments is made substantially equal to the antenna scan period AS.

The selection controller C2 can also perform at least one antenna scan process during the signal ON period by performing the scan repeat process according to the modification, as in the scan repeat process according to the above embodiments. The received strength of the antennas 206a to 206h can be reliably measured, by the antenna scan process performed during the signal ON period, and the antenna at a position capable of receiving the transmission signal can be detected, and the antenna having the largest strength can be detected.

After detecting the antenna having the largest strength by the scan repeat process, the selection controller C2 selects and switches the detected antenna having the largest strength as the receiving antenna for receiving the synchronization signal, to perform the synchronization search process as in the above embodiments.

The selection controller C2 can finish the scan repeat process and start the synchronization search process at a point in time when the antenna having the largest strength can be detected, that is, when the received strength of the antennas 206a to 206h can be reliably measured.

Figure 28:
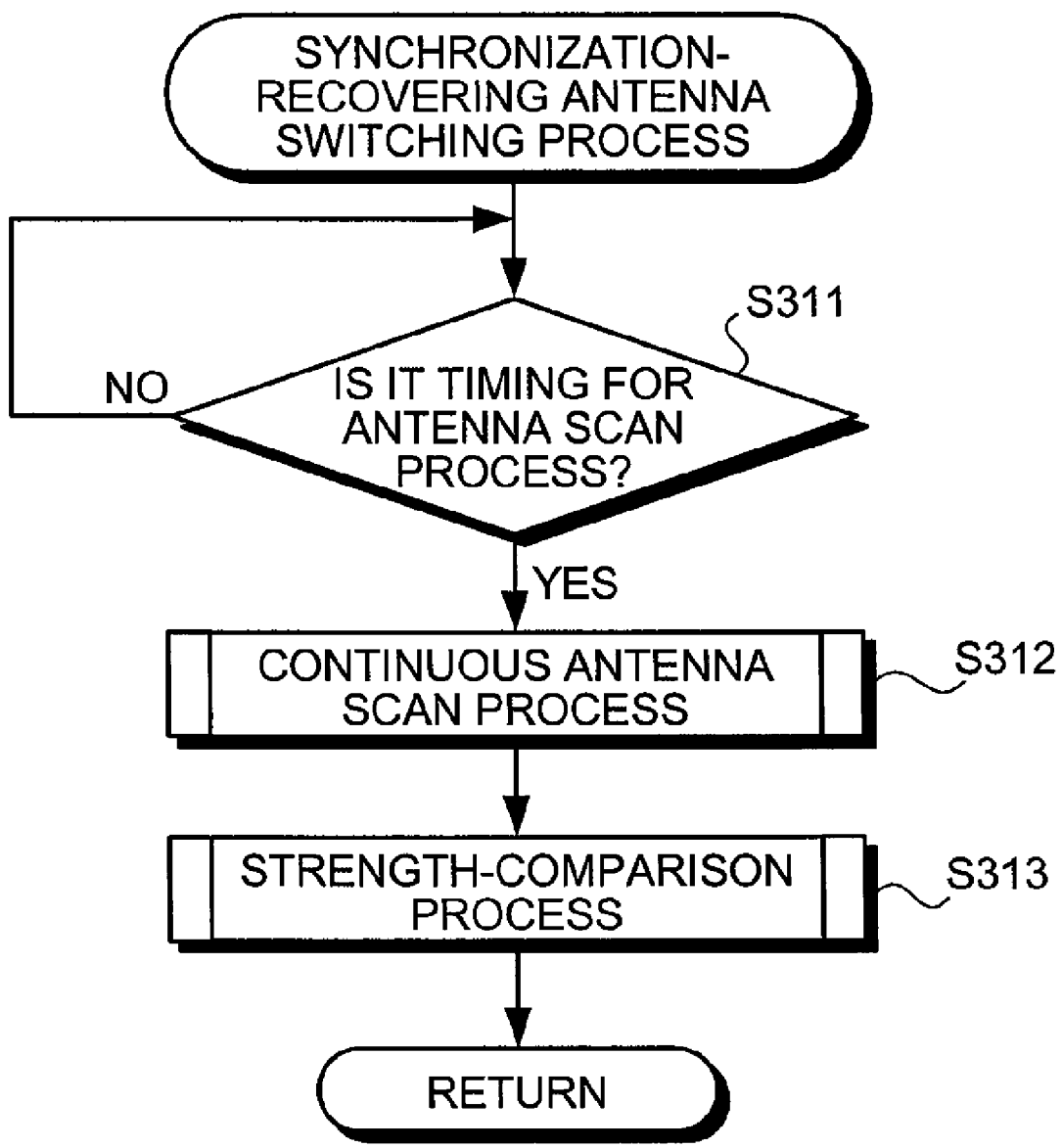
FIG. 28 is a flowchart of the synchronization-recovering-antenna switching process procedure as a modification example.

The synchronization-recovering-antenna switching process procedure according to the modification is explained with reference to a flowchart shown in FIG. 28. The synchronization-recovering-antenna switching process is executed at step S205 shown in FIG. 21. As shown in FIG. 28, the selection controller C2 determines whether it is a timing for the first antenna scan process in the scan repeat process based on the internal clock (step S311), and when it is not the timing for the antenna scan process (step S311: No), the selection controller C2 repeats the determination process and waits until the predetermined timing.

When it is the timing for the antenna scan process (step S311: Yes), the selection controller C2 executes the continuous antenna scan process for continuously performing the antenna scan process (step S312), and executes a strength comparison process for detecting the antenna having the largest strength by comparing the received strength of the respective antennas in the respective antenna scan process as the continuous scan process result (step S313), and returns to step S205.

Figure 29:
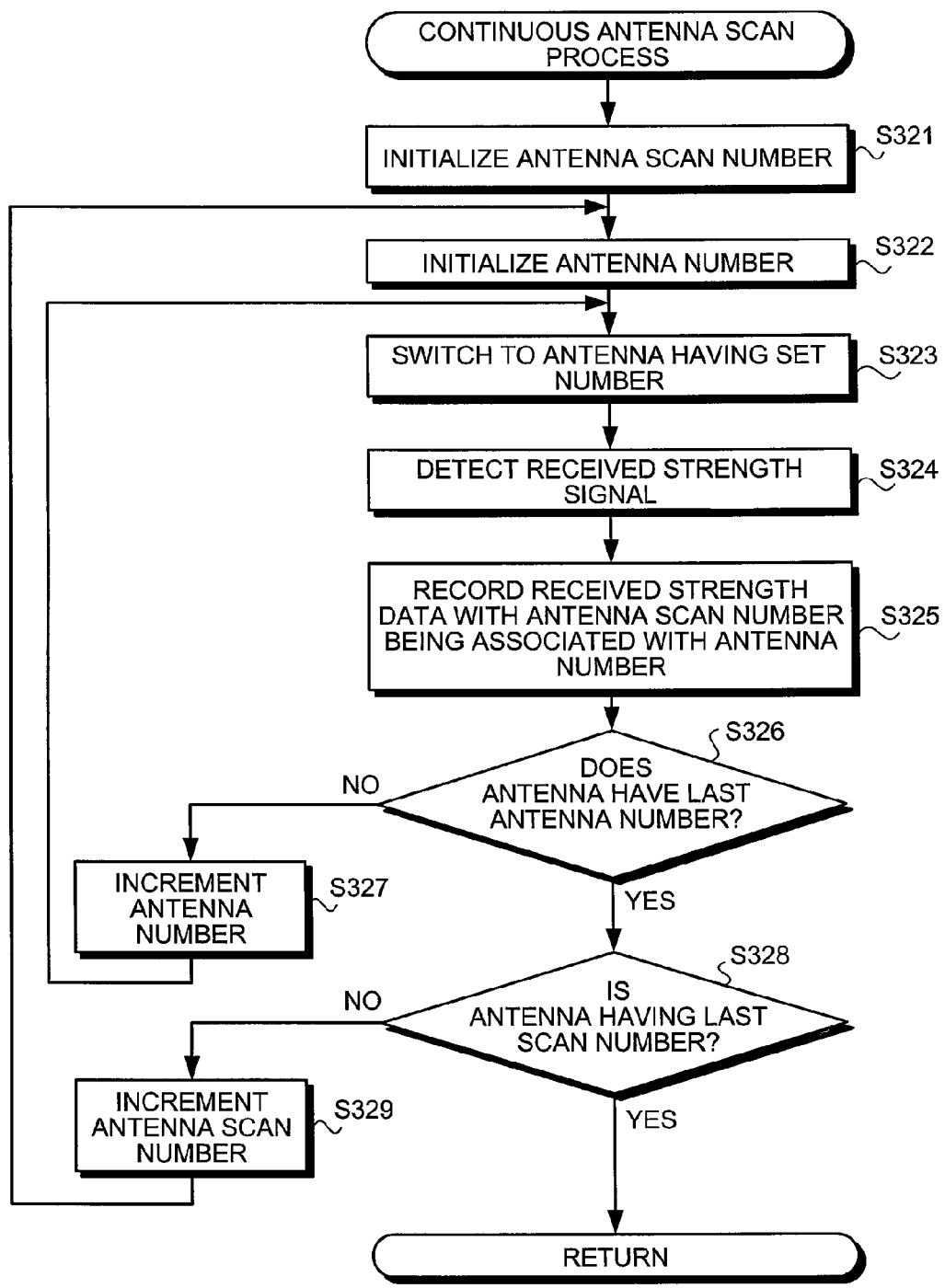
FIG. 29 is a flowchart of a continuous antenna scan process procedure shown in FIG. 28.

A continuous antenna-scan process procedure at step S312 is explained with reference to a flowchart shown in FIG. 29. As shown in FIG. 29, the switching controller C2c initializes the antenna number indicating the number of processes of the antenna scan process to be repetitively performed by the continuous antenna-scan process (step S321). The switching controller C2c selects and sets, for example, antenna No. 1 at step S321. The switching controller C2c also initializes the antenna number of the antenna to receive the signal first (step S322). The switching controller C2c selects and sets, for example, antenna No. 1 at step S322.

The switching controller C2c then switches the connection to the antenna having the antenna number set at step S322 (step S323), detects the received strength signal via the A/D converter 216 (step S324), and records the received strength data in the strength storage unit C2a, with the antenna scan number being associated with the antenna number (step S325).

The switching controller C2c then determines whether the connected antenna has the last antenna number, for example, antenna number No. 8 in the current antenna scan process (step S326). When the antenna does not have the last number (step S326: No), the switching controller C2c increments the antenna number (step S327), to repeat the processing from step S323.

On the other hand, when the antenna has the last number (step S326: Yes), the switching controller C2c determines whether the current antenna scan number is the last antenna scan number in the continuous antenna-scan process (step S328). When the antenna scan number is not the last antenna scan number (step S328: No), the switching controller C2c increments the antenna scan number (step S329), to repeat the processing from step S322. When the antenna scan number is the last antenna scan number (step S328: Yes), the switching controller C2c returns to step S312.

A strength comparison process procedure at step S313 shown in FIG. 28 is explained. The strength comparison process is performed as in the first strength comparison process shown in FIG. 24. However, in the strength comparison process, the antenna number sequentially switched as the compared antenna number is the respective antenna numbers in all the series of antenna scan processes, switched in the continuous antenna-scan process. In this case, for example, the received strength data is compared by sequentially switching from antenna number No. 1 of antenna scan number 1 to antenna number No. 8 of antenna scan number n in order of antenna number and in order of antenna scan number, to detect the antenna having the largest strength. For the data set in the Max register as the initial setting, for example, the data of antenna number No. 1 of antenna scan number 1 can be used.

In the third embodiment, as shown in FIG. 18, the antenna having the largest strength is detected by performing the antenna scan process during the received strength measurement period, and the detected antenna having the largest strength is designated as the receiving antenna in the image signal period, as the normal-antenna switching process when the synchronization signal is received. However, the process is not limited to the antenna switching process, and the processing can be performed, for example, as shown in a time chart in FIG. 30.

That is, in the antenna switching process shown in FIG. 30, the selection controller C2 measures the received strength of the antenna, for example, having antenna number No. 2 at a timing t1$_n$ in the received strength measurement period (IT) of the frame (n). The selection controller C2 also measures the received strength of the antenna having, for example, antenna number No. 1 at a timing t2$_n$ in the image signal period (VT) of the same frame (n). The selection controller C2 then compares these measured received strengths. When the received strength measured in the received strength measurement period exceeds the received strength measured in the image signal period, the selection controller C2 controls selection and switching of the antenna (for example, No. 2) measured in the received strength measurement period as the receiving antenna in the image signal period of the frame (n+1), which is the next frame. The selection controller C2 controls so as to repeat the antenna switching process while sequentially switching the antenna corresponding to the received strength measurement period for each frame.

Specifically, in FIG. 30, in frame (n), since the received strength of antenna number No. 2 does not exceed the received strength of antenna number No. 1, in frame (n+1), the receiving antenna in the image signal period is the same antenna number No. 1. On the other hand, the receiving antenna in the received strength measurement period in frame (n+1) is switched to antenna number No. 3. In frame (n+1), since the received strength of antenna number No. 3 exceeds the received strength of antenna number No. 1, in the next frame (n+2), antenna number No. 3 is selected and switched as the receiving antenna in the image signal period. At the same time, the receiving antenna in the received strength measurement period in frame (n+2) is switched to antenna number No. 4.

In the third embodiment and the modification thereof, it has been explained that the receiving device is applied to the wireless intra-subject information acquiring system, to receive the radio signal transmitted from the capsule endoscope. However, the present invention is not limited thereto, and the radio signal to be received can be an optional radio signal, so long as it is a signal having transmission information including at least the synchronization information transmitted at a predetermined transmission cycle, and a transmitting unit that transmits such a radio signal is not limited.

The first to the third embodiments and the modification described in the specification can be executed by combining each other, and an embodiment constructed by partially combining the first to the third embodiments and the modification is also included in the present invention.

INDUSTRIAL APPLICABILITY

The portable simplified image display apparatus and the receiving system according to the present invention are useful when an image based on a radio signal received by an integral antenna that receives radio signals transmitted from the body-insertable apparatus such as the capsule endoscope on a display unit, and are particularly, suitable for ensuring real-time observation in a state having strong received strength.

The invention claimed is:

1. A portable simplified image display apparatus, comprising:
    an integral antenna that receives a radio signal transmitted from a body-insertable apparatus to be introduced into a subject and outputs a first radio signal;
    a connector that is connectable to a receiving device, the receiving device including a set antenna which is arranged on a body surface of the subject and which receives the radio signal transmitted from the body-insertable apparatus to be introduced into the subject and outputs a second radio signal;
    a switch for switching between the first radio signal and the second radio signal, the second radio signal being received through the connector;
    a connection detector that controls switching of the switch for selecting one of the first and second radio signals to obtain a selected signal;
    a image processing circuit that performs image processing based on the selected signal to generate image data;
    a display unit that displays image data based on the image data generated by the image processing circuit;
    a strength detector that detects a received strength of the first radio signal transmitted from the body-insertable apparatus; and
    a notifying unit that notifies a state of the received strength detected, wherein
    the connection detector controls the switch to select the second radio signal when the receiving device is connected to the portable simplified image display apparatus through the connector, and to select the first radio signal when the receiving device is not connected to the portable simplified image display apparatus.

2. The portable simplified image display apparatus according to claim 1, wherein the notifying unit notifies the state of the received strength by visually changing the state of the received strength according to the received strength detected.

3. The portable simplified image display apparatus according to claim 2, wherein the notifying unit uses a part of the display unit, and notifies the state of the received strength in a predetermined display pattern changing depending on the received strength detected.

4. The portable simplified image display apparatus according to claim 2, wherein the notifying unit uses a light emission element, and notifies the state of the received strength in a predetermined light-on display pattern changing depending on the received strength detected.

5. The portable simplified image display apparatus according to claim 1, wherein the notifying unit notifies the state of received strength by aurally changing the state of received strength according to the detected received strength.

6. The portable simplified image display apparatus according to claim 1, comprising a built-in memory that stores image data according to the radio signal received.

* * * * *